(12) United States Patent
Schwartz et al.

(10) Patent No.: US 12,168,674 B1
(45) Date of Patent: Dec. 17, 2024

(54) REAGENTS AND METHODS FOR THE HIGHLY-EFFICIENT SYNTHESIS AND PURIFICATION OF BIOPOLYMERS

(71) Applicant: OLIGO FOUNDRY, INC., Encinitas, CA (US)

(72) Inventors: David A. Schwartz, Encinitas, CA (US); Jimmy H. Williams, Santee, CA (US)

(73) Assignee: Oligo Foundry, Inc., Encinitas, CA (US)

( * ) Notice: Subject to any disclaimer, the term of this patent is extended or adjusted under 35 U.S.C. 154(b) by 0 days.

(21) Appl. No.: 18/534,413

(22) Filed: Dec. 8, 2023

(51) Int. Cl.
*C07H 19/10* (2006.01)

(52) U.S. Cl.
CPC .................................. *C07H 19/10* (2013.01)

(58) Field of Classification Search
CPC ...................................................... C07H 19/10
See application file for complete search history.

(56) References Cited

U.S. PATENT DOCUMENTS

| | | | |
|---|---|---|---|
| 4,725,677 | A | 2/1988 | Koster et al. |
| 5,410,068 | A | 4/1995 | Coull et al. |
| 5,586,586 | A | 12/1996 | Fiech |
| 5,874,532 | A | 2/1999 | Pieken et al. |
| 6,001,966 | A | 12/1999 | Pieken et al. |
| 6,586,586 | B1 | 7/2003 | Krotz et al. |
| 6,800,728 | B2 | 10/2004 | Schwartz |
| 7,102,024 | B1 | 9/2006 | Schwartz et al. |
| 10,087,208 | B2 | 10/2018 | Guzaev et al. |
| 10,669,301 | B2 | 6/2020 | Guzaev et al. |
| 10,954,266 | B2 | 3/2021 | Zitterbart et al. |
| 2008/0221343 | A1 | 9/2008 | Schwartz et al. |

FOREIGN PATENT DOCUMENTS

| | | |
|---|---|---|
| EP | 0424819 B1 | 12/1994 |
| WO | 2001070685 A2 | 9/2001 |
| WO | 2002010431 A2 | 2/2002 |
| WO | 2002010432 A2 | 2/2002 |
| WO | 2002057422 A2 | 7/2002 |
| WO | 2008140452 A1 | 11/2008 |
| WO | 2011100493 A1 | 8/2011 |
| WO | 2012047639 A2 | 4/2012 |
| WO | 2012071428 A2 | 5/2012 |
| WO | 2013177046 A1 | 11/2013 |
| WO | 2016127149 A2 | 8/2016 |
| WO | 2018017606 A1 | 1/2018 |

OTHER PUBLICATIONS

Definition of derivative, Oxford English Dictionary, http://dictionary.oed.com, accessed online on May 20, 2010. (Year: 2010).*
Shchepinov et al., Tetrahedron, 2000, 56, p. 2713-2724. (Year: 2000).*
Jaschke et al., Nucleic Acids Research, 1994, 22(22), p. 4810-4817. (Year: 1994).*
Andrews et al. (2021) J. Org. Chem. 86:49-61.
Beaucage et al. (1981) Tet. Lett. 22:1859.
Bargh et al. (2019) Chem. Soc. Rev. 48:4361-74.
Baskin et al. (2007) Proc. Natl Acad. Sci. U.S.A. 104:16793-97.
Dirksen et al. (2006) Angew. Chem. 45:7581-7584 (DOI: 10.1002/anie.200602877.
Ellington et al. (2000) Introduction to the Synthesis and Purification of Oligonucleotides in Current Protocols in Nucleic Acid Chemistry A.3C.1-A.3C.22.
Evans (2007) Aus. J. Chem. 60:384-395.
He et al. (2021) Chem. Commun. 57:4263.
He et al. (2021) Current Protocols 1:e247 (doi: 10.1002/cpz1.247).
Hoose et al. (2023) Nature Rev. Chem. 7:144 (doi: 10.1038/s41570-022-00456-9).
Horn et al. (1986) Tetrahedron Lett. 27:4705-4708.
Igata et al. (2017) Bioorg. Med. Chem. 25:5962-5967.
Karver et al. (2011) Bioconjugate Chem. 22:2263-70.
Kolb et al. (2001) Angew. Chem. Int. Ed. Engl. 40:2004-2021.
Leriche et al. (2012) Bioorg. Med. Chem. 20:571-582.
Lönnberg (2017) Beilstein J. Org. Chem. 13:1368-1387.
McClain et al. (2023) Handbook of Chemical Biology of Nucleic Acids (doi: 10.1007/978-981-16-1313-5_84-1).
Paul et al. (2023) Molecules 28:5380.
Stöckmann et al. (2011) Org. Biomol. Chem. 9:7303.
Tu et al. (2019) ChemBioChem 20:1615-1627.
York et al. (2011) Nucl. Acids Res. 40 e4 (doi: 10.1093/nar/gkr910).
Zitterbart et al. (2021) Chem. Sci. 12:2389.

* cited by examiner

*Primary Examiner* — Jonathan S Lau
(74) *Attorney, Agent, or Firm* — David A. Roise; VLP Law Group LLP

(57) ABSTRACT

The present disclosure provides reagent compounds, reactive biopolymeric compounds, and methods of making and using these materials for the rapid and efficient synthesis and purification of biopolymeric compounds at low cost. The materials and methods yield highly pure synthetic biopolymeric compounds, including synthetic oligonucleotides and polypeptides, and reduce or eliminate the need for toxic solvents in the synthetic process.

21 Claims, 18 Drawing Sheets

Target Mass Summary

| RT (min) | Target Mass (Da) | Observed Mass (Da) | Mass Error | Intensity | % Abundance (in Spectrum) | %Purity (Estimate) | Identity | Result Code |
|---|---|---|---|---|---|---|---|---|
| 0.332 | 7239.0 | 7239.4 | 0.4 Da (0.006 %) | 7.82E+005 | 78.48 | 78.48 | Target Mass | G |

Chromatogram Summary

| RT (min) | Base Peak Mass (Da) | Intensity | Spectral Quality | LC/MS Peak Area | LC/MS Area Percent |
|---|---|---|---|---|---|
| 0.332 | 7239.4 | 7.82E+005 | ok | 3.45E+007 | 100.00 |

FIG. 3A

Target Mass Summary

| RT (min) | Target Mass (Da) | Observed Mass (Da) | Mass Error | Intensity | % Abundance (in Spectrum) | %Purity (Estimate) | Identity | Result Code |
|---|---|---|---|---|---|---|---|---|
| 0.332 | 7543.0 | 7543.7 | 0.7 Da (0.009 %) | 1.25E+006 | 93.51 | 94.58 | Target Mass | G |

Chromatogram Summary

| RT (min) | Base Peak Mass (Da) | Intensity | Spectral Quality | LC/MS Peak Area | LC/MS Area Percent |
|---|---|---|---|---|---|
| 0.332 | 7543.7 | 1.25E+006 | ok | 3.28E+007 | 100.00 |

FIG. 4A

REAGENTS AND METHODS FOR THE HIGHLY-EFFICIENT SYNTHESIS AND PURIFICATION OF BIOPOLYMERS

BACKGROUND OF THE INVENTION

The fields of molecular biology and biotechnology have been fundamentally transformed by the advent of synthetic biopolymers, including synthetic oligonucleotides and polypeptides. These short, synthetic fragments of nucleic acids and proteins serve as indispensable tools in a wide array of applications. In the case of synthetic oligonucleotides, these applications range from gene synthesis, PCR, and DNA sequencing to the critical roles of the molecules in molecular diagnostics and therapeutic interventions. The effectiveness and safety of these applications, particularly in high-stakes areas like therapeutics and diagnostics, are inextricably linked to the purity of the synthetic biopolymers.

The cornerstone of current oligonucleotide and polypeptide production is the solid-phase synthesis method. This approach typically involves the sequential addition of monomeric units, for example phosphoramidite nucleoside monomers for oligonucleotide synthesis and activated amino acid monomers for polypeptide synthesis, to a growing chain affixed to a solid support. The monomers are designed to include a range of natural and unnatural bases, backbones, and sidechains, catering to the diverse requirements of various applications. The process involves a series of cycles: coupling, where a new monomer is added; capping, to prevent unreacted sites from reacting in subsequent cycles; deblocking, removing specific protecting groups from the newly added monomer to allow subsequent chain elongation; and finally, cleavage from the solid support, which may or may not involve final deprotection.

In solid phase oligonucleotide synthesis specifically, the process involves elongating the polymer, typically from the 3' terminus to the 5' terminus, via a series of cycles: deblocking, removing the 5'-O-dimethoxytrityl protecting group, commonly referred to as a trityl or DMT group, from the support-bound nucleoside or oligonucleotide to allow chain elongation; coupling, addition of the next monomeric unit to extend the chain by one nucleoside residue; capping, reacting the support-bound oligonucleotide with a reagent, such as acetic anhydride, to eliminate sites left unreacted due to incomplete coupling with the most recently added monomer; and oxidation, converting phosphite linkages to the more stable phosphotriester linkages. This cycle is repeated according to the number of nucleoside residues in the oligonucleotide chain. Monomers are prepared with a trityl protecting group to prevent their polymerization in solution and to limit the coupling reaction to addition of a single monomer. Once the final monomer is coupled and the chemical synthesis of the oligonucleotide is completed, the products are cleaved from the solid support, which may or may not involve final deprotection. In practice, coupling efficiency is typically no greater than 99% while capping efficiency may exceed 99.9%. Due to incomplete coupling and capping of the unreacted sites to terminate the polymer, truncated failure sequences accumulate during each cycle of synthesis. Many practical oligonucleotides, such as those formed for use in diagnostics and therapeutics, require twenty or more cycles of monomer addition. With increasing cycles, the full-length oligonucleotide represents a diminishing fraction of the total polymer that is released during the cleavage step, with the remainder comprised of a heterogeneous mixture of chemically similar but prematurely truncated oligonucleotides, commonly denoted N-1, N-2, etc.

Despite its widespread adoption, the solid-phase synthetic method encounters limitations in scalability and efficiency, particularly for oligonucleotides and polypeptides with modified chemistries or unconventional backbones.

Given these considerations, a significant challenge in solid phase oligonucleotide synthesis is to isolate the full-length oligonucleotide from the truncated failure sequences that are also cleaved from the support. For this purpose, the so-called trityl-on or DMT-ON purification method is a widely recognized technique, notable for its value in favoring the purification of full-length oligonucleotides. This method depends on retaining the final trityl protecting group attached to the 5' terminus during the final cycle of monomer addition to complete the chemical synthesis of an oligonucleotide. The differential purification strategy hinges on the presence of the trityl group on full-length oligonucleotides, as opposed to its absence on truncated failure sequences.

The differential purification process typically employs reversed-phase chromatographic techniques, where oligonucleotides with the trityl group are selectively adsorbed onto hydrophobic chromatographic media. This selective binding, driven by the hydrophobic nature of the trityl group, facilitates the separation of full-length oligonucleotides from truncated sequences and other impurities. Oligonucleotides are eluted from the chromatographic media in two main ways. The first method elutes oligonucleotides with the trityl group still attached, necessitating subsequent deblocking for functionality. The second approach combines deblocking with elution, producing immediately usable oligonucleotides and streamlining the process. In principle, either approach offers the potential to obtain a solution of purified, full-length oligonucleotide after a single adsorption and elution process.

Numerous commercial kits, including the Glen-Pak system (see www.glenresearch.com), have been developed based on the trityl-on method. These kits typically feature specialized cartridges designed for the efficient binding of trityl-protected oligonucleotides, offering scalable purification suitable for laboratory-scale synthesis.

However, a significant limitation of the trityl-on method, and its commercial variants like the Glen-Pak system, arises from the limited selectivity for trityl-protected oligonucleotides over the truncated failure oligonucleotides. All oligonucleotides carry hydrophobic moieties that, even in the absence of a trityl group, may lead to non-specific binding to the reversed-phase media. This phenomenon can result in the incomplete removal of failure sequences, which is particularly problematic for longer oligonucleotides, where the full-length product represents only a minor fraction of the material eluted from the solid support during the cleavage step. This issue further complicates the purification process, especially in scenarios where a high degree of purity is essential.

Although trityl-on purification, including systems like the Glen-Pak, is satisfactory for general purposes, it is not adequate for situations demanding the highest level of oligonucleotide purity. For small scale syntheses, purification of fully deprotected oligonucleotides by polyacrylamide gel electrophoresis (PAGE) may be satisfactory. For applications requiring both large scale synthesis and maximum oligonucleotide purity, such as diagnostic or therapeutic applications, high-performance liquid chromatography (HPLC) methodologies are typically applied. Both PAGE and HPLC are limited by challenges such as lower yields, high expense, and the production of additional chemical waste compared to the trityl-on approach. In particular, elution of oligonucleotides in HPLC produces large volumes of mixtures of aqueous buffers with organic solvents such as acetonitrile, providing increased costs and environmental impacts.

A particular challenge in these areas is the need for rapid, on-demand synthesis of a large array of high-quality oligonucleotides for gene synthesis. This requirement underscores the necessity for an innovative approach in oligonucleotide synthesis and purification. Furthermore, deblocking of the 5'-O-dimethoxytrityl (5'-O-DMT) group during solid-phase oligonucleotide synthesis requires strong acids such as dichloroacetic acid (DCA) and trichloroacetic acid (TCA), and it is known in the art that these treatments can result in the depurination of previously incorporated purine nucleotides. See, e.g., Ellington et al. (2000) Introduction to the Synthesis and Purification of Oligonucleotides in *Current Protocols in Nucleic Acid Chemistry* A.3C.1-A.3C.22. As a result of this chemical damage, the assembled gene may display a sequence that differs from that desired. A reagent, such as a modified trityl group, that can be removed under mild acid conditions and that does not result in depurination would also be of significant value.

In therapeutic applications, the role of oligonucleotides is increasingly prominent, particularly with the incorporation of modified bases and backbones. These modifications are essential for enhancing an oligonucleotide's stability, specificity, and uptake, each of which is crucial for therapeutic efficacy. However, the synthesis and purification of these modified oligonucleotides are fraught with challenges, demanding high levels of precision and efficiency. In particular, the monomer coupling efficiency may drop well below 99%, exacerbating the challenge of separating full-length product from truncated failure sequences.

Looking beyond current uses, the potential of oligonucleotides in emerging fields such as synthetic biology, agriculture, medical therapy, diagnostics, and data storage is immense. Synthetic biology relies on oligonucleotides for constructing synthetic gene networks, enabling the programming of cellular functions. In agriculture, synthetic oligonucleotides are instrumental in developing genetically enhanced crops. In medical therapy, synthetic oligonucleotides are at the forefront of novel treatments like gene therapy and personalized medicine. For diagnostics, synthetic oligonucleotides are key in developing more sensitive and accurate disease detection methods.

U.S. Pat. No. 5,410,068 describes compounds and methods for the attachment of functional groups to natural products, including oligonucleotides. The patent discloses a synthetic oligonucleotide comprising a 5'-O-DMT group modified with an N-hydroxysuccinimidyl (NHS) group. The NHS group can be used to functionalize the oligonucleotide with compounds comprising primary amines, but the reaction is not selective nor is it reversible. The NHS group is also not stable to the conditions typically used to cleave synthetic oligonucleotides from the synthesis resin (e.g., concentrated ammonium hydroxide), so oligonucleotides released from the resin by standard cleavage conditions are no longer reactive.

U.S. Pat. No. 5,586,586 describes methods and compounds useful for the purification of oligonucleotides and their analogues. The methods and compounds facilitate removal of oligonucleotides having abasic sites by formation of imine linkages with the contaminants.

PCT International Publication No. 2012/047639 describes methods for purifying synthetic oligonucleotides and novel capping agents. The methods comprise, for example, capping, polymerizing, and separating failure sequences or reacting full-length oligonucleotides with a compound to attach a polymerizable functional group to an end of the full-length oligonucleotides, polymerizing the full-length oligonucleotides, and removing failure sequences to recover the full-length oligonucleotides. The capping agents comprise a polymerizable functional group.

York et al. (2011) *Nucl. Acids Res.* 40 e4 (doi: 10.1093/nar/gkr910) describe a highly-parallel method for the purification and functionalization of 5'-labeled oligonucleotides. The method utilizes oligonucleotides functionalized with a 5'-aldehyde group to generate 5'-hex-Histidine-labeled oligonucleotides that can be purified using a nickel resin. The 5'-hex-Histidine label is then exchanged for a biotin label, and the biotin-labeled oligonucleotides are used in targeted sequencing applications.

Zitterbart et al. (2021) *Chem. Sci.* 12:2389 and U.S. Pat. No. 10,954,266 describe reagents and methods for the purification of synthetic peptides using a reductively-cleavable linker system.

Despite these and other advances, there is a need in the art for new and improved reagents and methods for the preparation and purification of synthetic biopolymers of any chemistry with high purity and yield. Such strategies can revolutionize the production process and expand the potential applications of biopolymers in various sectors.

SUMMARY OF THE INVENTION

The present disclosure addresses these and other needs by providing in one aspect a reagent compound having a structure:

wherein T' is a modified trityl protecting group comprising a selectively-reactive linker moiety, C' is a connecting moiety, and P' is a phosphoramidite or phosphoramidate.

In some embodiments, T' has a structure:

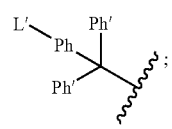

wherein L' includes the selectively-reactive linker moiety, Ph is an optionally substituted phenylene moiety, and each Ph' is independently an optionally substituted phenyl group.

In some embodiments, each Ph' is independently substituted with one or more $C_1$-$C_4$ alkoxy groups, one or more $C_1$-$C_4$ alkyl groups, or a combination of $C_1$-$C_4$ alkoxy groups and $C_1$-$C_4$ alkyl groups.

In some embodiments, the reagent compound has a structure:

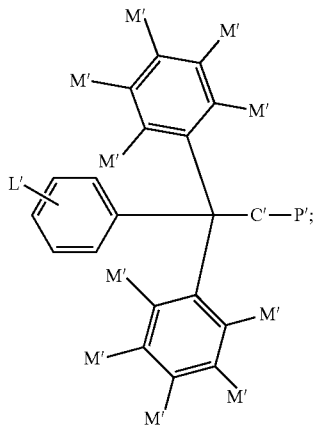

wherein each M' is independently a $C_1$-$C_4$ alkoxy group, a $C_1$-$C_4$ alkyl group, —H, or a combination thereof.

In some embodiments, the reagent compound has a structure:

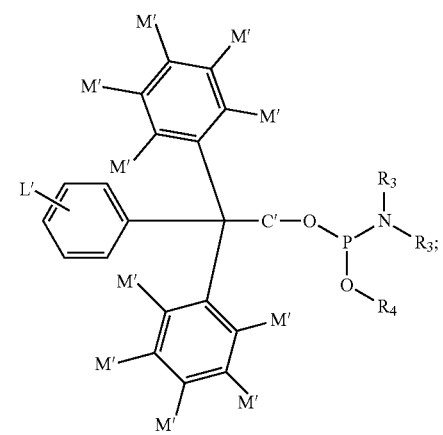

wherein each $R_3$ is independently a $C_1$-$C_6$ alkyl group, and $R_4$ is an optionally-substituted $C_1$-$C_6$ alkyl group or a saccharide-substituted polyethylene glycol group.

In some embodiments, the reagent compound has a structure:

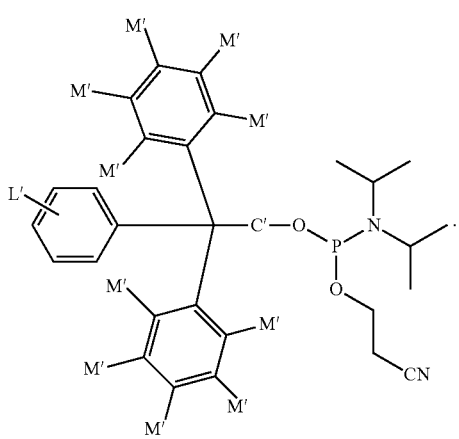

In some embodiments, at least one M' is a methoxy group.

In some embodiments, the reagent compound has a structure:

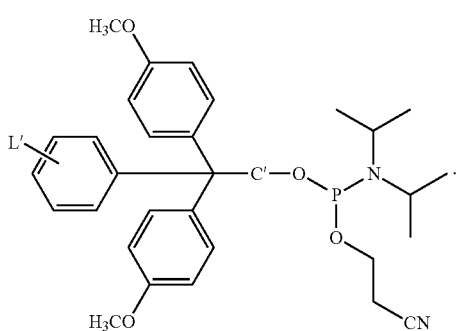

In some embodiments, the connecting moiety of the reagent compound includes a nucleoside residue, a locked nucleoside residue, a morpholino nucleoside residue, a polyethylene glycol residue, or a linker residue. More specifically, the connecting moiety can include a nucleoside residue or a locked nucleoside residue.

In some embodiments, the reagent compound has a structure:

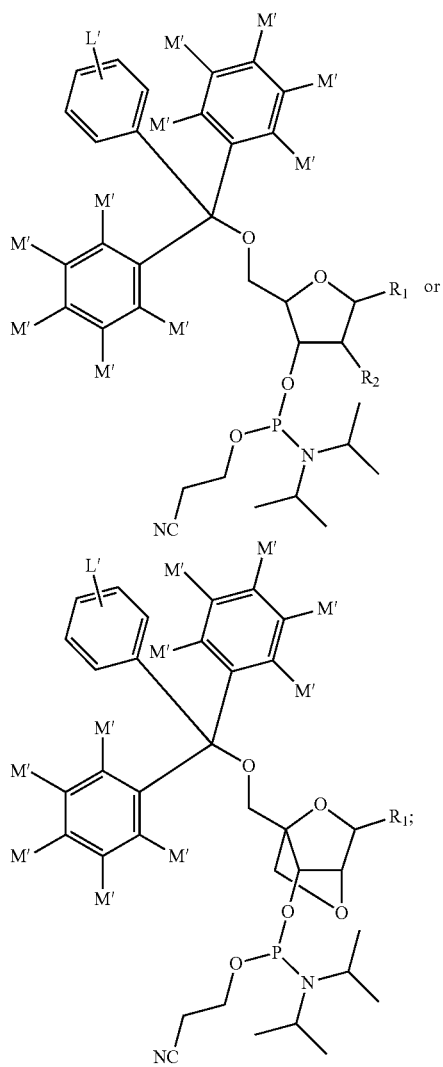

wherein $R_1$ is —H, a nucleobase, a protected nucleobase, or a modified nucleobase, and $R_2$ is —H, -hydroxyl, protected -hydroxyl, modified -hydroxyl, or -halo. More specifically, $R_2$ is —H, -hydroxyl, protected -hydroxyl, —OCH$_3$,

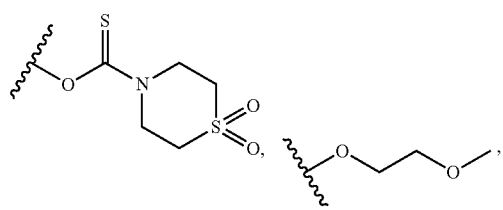

In some embodiments, the connecting moiety of the reagent compound includes a linker residue. More specifically, the linker residue can include an optionally substituted —C$_{1-8}$-alkanediyl-, wherein each carbon atom is optionally replaced with an optionally substituted heteroatom. Even more specifically, the linker residue can include:

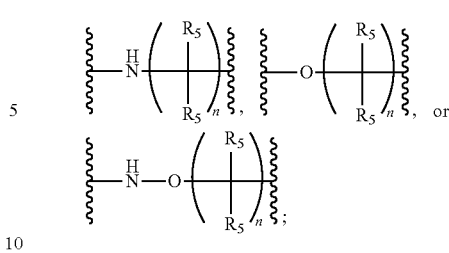

wherein n is 1-6 and each $R_5$ is independently —H, C$_{1-3}$-alkyl, C$_{1-3}$-carboxylate, C$_{1-3}$-alkyl-C$_{1-3}$-carboxylate, C$_{1-3}$-alkoxy, -halo, -nitro, -amino, -amido, or -hydroxyl, or can include

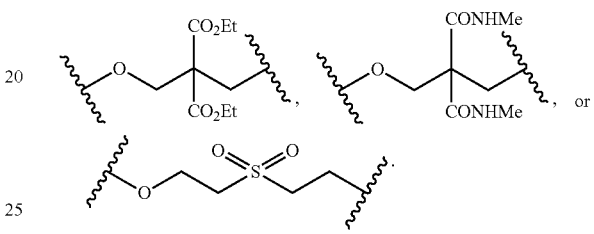

In some embodiments, the connecting moiety of the reagent compound includes a polyethylene glycol residue.

In some embodiments, the selectively-reactive linker moiety of the reagent compound includes a reactive carbonyl group, a reactive oxyamino group, a reactive hydrazino group, a component of a click reaction, or a derivative of any thereof. More specifically, the selectively-reactive linker moiety can include:

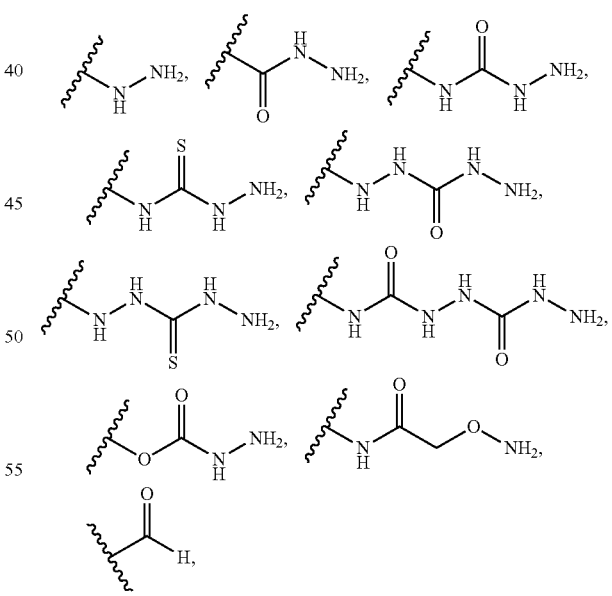

or a derivative of any thereof.

BRIEF DESCRIPTION OF THE DRAWINGS

FIG. 3A. Mass spectrometric purity analysis of a desalted unbound oligonucleotide.

FIG. 4A. Mass spectrometric purity analysis of a desalted purified oligonucleotide.

DETAILED DESCRIPTION OF THE INVENTION

Figure 1A:
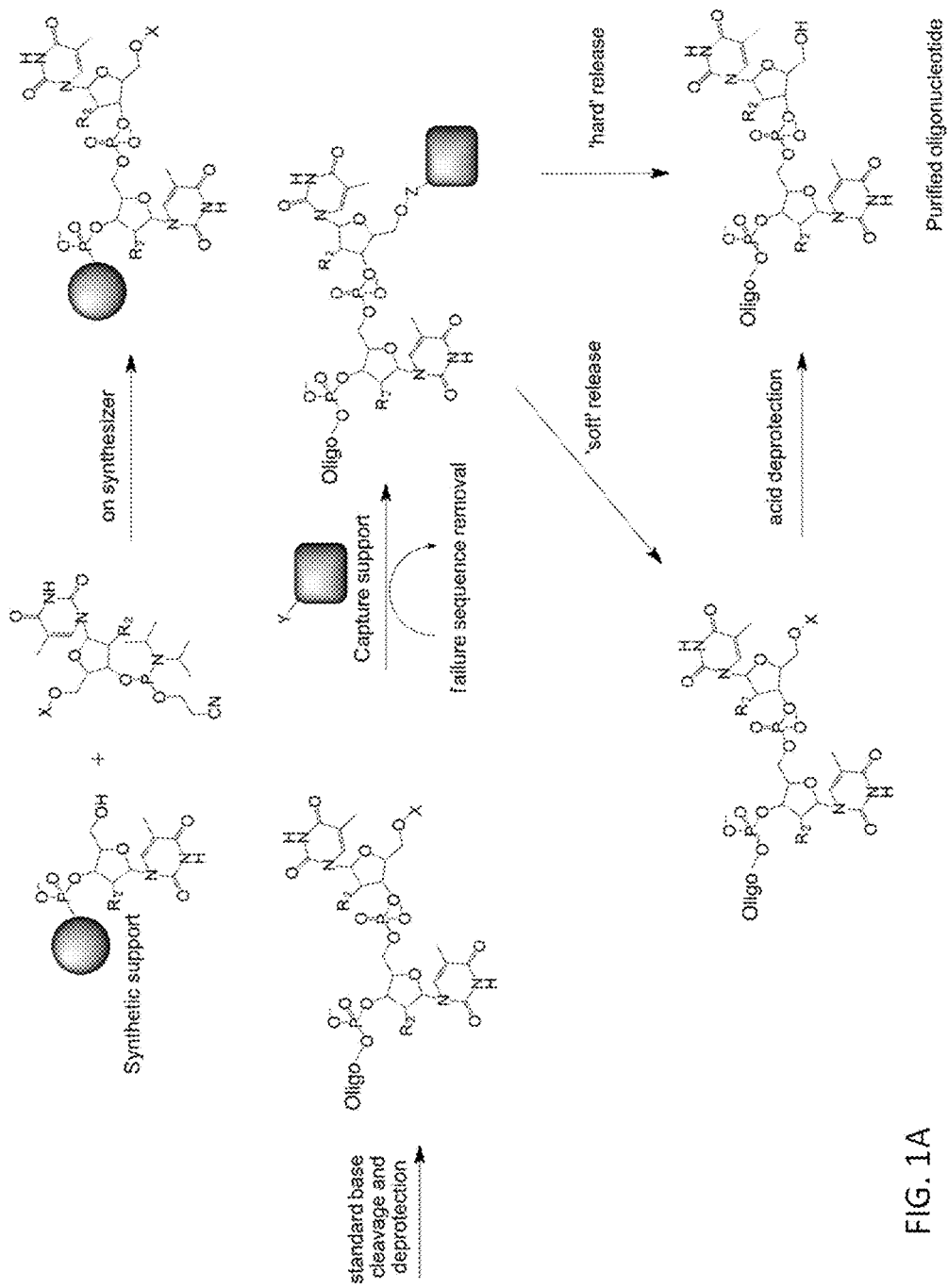
FIG. 1A illustrates an exemplary general scheme for the capture and release of a synthetic oligonucleotide comprising a first selectively-reactive linker moiety on the 5'-terminus and a capture support comprising a complementary second selectively-reactive linker moiety.

Described herein are technologies that simultaneously increase yields of purified synthetic biopolymeric compounds, shorten the time required to produce higher purity products, reduce the costs associated with synthesis and purification of those products, allow higher throughput biopolymeric compound syntheses, and reduce or eliminate the use of toxic solvents in the purification of the synthetic biopolymeric compounds. In particular, described herein are reagents and methods for use in the capture and release of biopolymeric compounds, particularly synthetic biopolymeric compounds. These reagents and methods facilitate the synthesis and purification of biopolymeric compounds at small and large scales, with extremely high purity, and in good yields.

Reagents of the disclosure are designed to include novel trityl protecting groups, including dimethoxytrityl (DMT) groups, that have been modified to contain an electron withdrawing group. Such groups include, but are not limited to, aldehydes, ketones, and carboxylic acids that can be deprotected using mild aqueous acid conditions. Deprotection of an unmodified 5'-O-DMT group during traditional solid phase oligonucleotide synthesis requires the use of strong acids, such as dichloroacetic acid (DCA) and trichloroacetic acid (TCA). These treatments can result in the depurination of purine-containing nucleotides. See, e.g., U.S. Pat. No. 6,586,586. The use of modified trityl protecting groups in the solid-phase synthesis of biopolymeric compounds enables the deprotection of the synthetic compounds under milder conditions, thus resulting in fewer side-reactions and higher purity of the resulting compounds.

In general terms, the reagents and methods disclosed herein relate to a capture and release technology ("C&R technology"), wherein a selectively-reactive linker moiety is incorporated into a protecting group on a terminal residue of a biopolymeric compound, preferably a synthetic biopolymeric compound. For example, the DMT group, which is typically used to protect the 5' end of a growing synthetic oligonucleotide in traditional solid-phase oligonucleotide synthesis, can be modified to include the selectively-reactive linker moiety.

It should also be understood, however, that although the novel reagents and methods disclosed herein have been demonstrated using traditional solid-phase oligonucleotide synthetic methods, which typically employ a DMT protecting group on the 5' terminus of the synthetic oligonucleotide, the modified trityl protecting groups of the instant disclosure can be used as protecting groups on any suitable residue of any suitable synthetic biopolymeric compound, so long as the modified trityl protecting group remains covalently associated with the synthetic biopolymeric compound following cleavage of the compound from the synthetic support, as would be understood by those of ordinary skill in the art. For example, a 3'-protected nucleoside phosphoramidite can have the following structure:

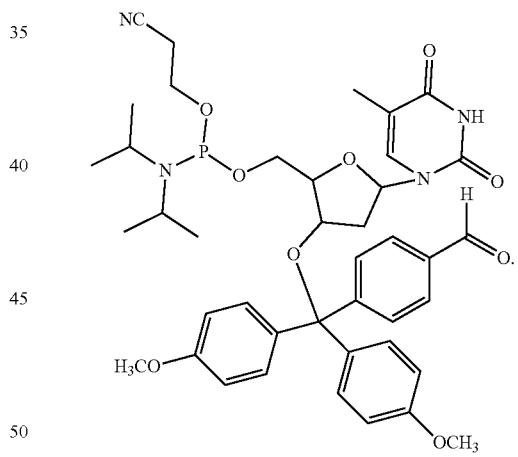

After cleavage of the synthetic biopolymer from the synthetic support, the selectively-reactive linker moiety that is attached to the trityl protecting group of the full-length synthetic biopolymeric compound can be selectively captured using a solid phase capture support that includes a complementary selectively-reactive linker capable of forming a covalent bond with the selectively-reactive linker of the modified trityl protecting group.

After selective capture of the full-length synthetic product on the capture support, failure sequences can be removed by one or more simple aqueous washing steps. The purified, full-length synthetic biomolecule can then be released from the capture support, either by cleavage of the modified trityl protecting group from the biomolecule, using appropriate de-tritylation conditions (i.e., "hard release"), or by selectively cleaving the covalent bond formed between the two selectively-reactive linker moieties (i.e., "soft release"). See, e.g., FIGS. 1A and 1B. The capture and release technologies disclosed herein can be used either as an alternative to, or in addition to, the techniques for purification of synthetic oligonucleotides and other synthetic biopolymeric compounds that are used traditionally. See, e.g., Andrews et al. (2021) *J. Org. Chem.* 86 49-61.

The just-described approach provides a number of advantages over methods currently known in the art. For example, the complete capture and release protocol can be performed in aqueous media, thus obviating the need for costly equipment and organic solvents, each of which can be subject to supply-chain limitations. The approach thereby also significantly reduces costs of the synthetic process and increases reliability. The elimination of toxic solvents, such as acetonitrile, from the purification workflow increases yield and reflects a significant step forward in the pursuit of more environmentally favorable purification technologies. As has been reported recently, the purification process stage can be responsible for roughly half of the overall process mass intensity (PMI) required in the manufacture of therapeutic oligonucleotides. See, e.g., Andrews et al. (2021) *J. Org. Chem.* 86 49-61.

In more detail, some of the steps involved in accomplishing the above synthetic goals include (1) synthesis of reagents comprising selectively-reactive linker moieties, such as modified trityl protecting groups, (2) incorporation of those reagents into modified reagent compounds, for example modified phosphoramidite or phosphoramidate reagent compounds comprising linker residues, phosphorylation reagents, or nucleoside residues, (3) incorporation of those modified reagent compounds into synthetic biopolymeric compounds, for example synthetic oligonucleotides, in the final step of a solid-phase synthesis, whereby only the desired, uncapped, full-length product will react with the modified reagent compound, (4) modification of a capture support to incorporate a selectively-reactive linker moiety complementary to the selectively-reactive linker moiety associated with the modified biopolymeric compound, (5) capture of the full-length reactive biopolymeric compound by the modified capture support via covalent bond formation, (6) washing of the captured full-length biopolymeric compound to remove failure sequences and other contaminants, and (7) release of the purified biopolymeric compound from the capture support.

In some embodiments, the novel reagent compounds of the instant disclosure can be used to generate oligonucleotides that are useful in gene syntheses. For example, a chemical phosphorylation reagent comprising a selectively-reactive linker moiety on a modified trityl protecting group can be used to incorporate a phosphate at the 5'-terminus of a synthetic oligonucleotide. Incorporation of the phosphate and purification of a terminal phosphate-incorporated oligonucleotide can be demonstrated, for example by LC-MS. After purification, the 5'-phosphorylated oligonucleotide can be ligated to a 3'-OH oligonucleotide using standard methods.

In some embodiments, the C&R technology employs Schiff base chemistry, wherein an acid-labile protecting group on the terminal residue of a synthetic biopolymeric compound can be modified to incorporate a carbonyl moiety or derivative, for example an aliphatic or aromatic aldehyde or ketone group, or derivative. Alternatively, the acid-labile protecting group on the terminal residue of the synthetic biopolymeric compound can be modified to incorporate an amino moiety or derivative, for example an aliphatic or aromatic amine, hydrazine, hydrazide, carbazide, thiosemicarbazide, or oxyamino group, or derivative. A capture support for the reactive synthetic biopolymeric compound can be prepared by modifying a suitable solid support with a second Schiff base component that is complementary to the carbonyl or amino moiety on the reactive biopolymeric compound. These approaches can be adapted for the synthesis of biopolymeric compounds possessing terminal linker moieties such as, but not limited to, amino, thiol, aminooxy, or azido groups, as well as detectable moieties, such as fluorophores.

In some embodiments, the C&R technology employs a "click" reaction, wherein a selectively-removable protecting group on the terminal residue of a synthetic biopolymeric compound can be modified to incorporate a first component of a click reaction. In these embodiments, the solid support used to capture the synthetic biopolymer contains a second component of the click reaction that is chosen to specifically and efficiently react with the first component of the click reaction, as would be understood by those of ordinary skill in the art. Further details regarding the use of click chemistry in the C&R technology will be provided below.

FIG. 1A shows an exemplary series of reactions that illustrate, in general, the capture and release concepts with a modified trityl protecting group in a traditional solid-phase oligonucleotide synthetic process. In this reaction scheme, the top reaction ("on synthesizer") shows the extension of a 5'-deblocked, support-bound, synthetic oligonucleotide by reaction with a modified nucleoside phosphoramidite. Specifically, the "X" group on the phosphoramidite represents a modified trityl protecting group that comprises a selectively-reactive linker moiety, as will be defined in further detail below, and the "$R_2$" groups on the oligonucleotide and the nucleoside phosphoramidite can be either a hydrogen (for a 2'-deoxyribose phosphoramidite) or a hydroxyl group, a protected hydroxyl group, or a modified hydroxyl group (for a 2'-ribose phosphoramidite). The "synthetic support", as represented by a shaded sphere in the drawing, can be any suitable synthetic support, for example a controlled pore glass (CPG) or a microporous polystyrene (MPPS) synthetic support. Although synthetic supports have traditionally been composed of solids, soluble supports are equally suitable. See, e.g., Lönnberg (2017) *Beilstein J. Org. Chem.* 13 1368-1387. Details of the methods and reagents traditionally used in standard oligonucleotide synthesis, including any additional steps not explicitly specified herein, are well known in the art. See, e.g., Andrews et al. (2021) *J. Org. Chem.* 86 49-61.

In the next step, the completed oligonucleotide (designated as "Oligo") is released from the synthetic support under conditions where the modified trityl protecting group remains associated with the 5'-end of the oligonucleotide, and the oligonucleotide is therefore a "reactive oligonucleotide". Specifically, the selectively-reactive linker moiety on the oligonucleotide is available to react with a complementary selectively-reactive linker moiety on a "capture support" (represented as the shaded cube in the drawing, where the "Y" group comprises the complementary selectively-reactive linker moiety). Selective reaction of the two complementary selectively-reactive linker moieties results in a covalent linker adduct (represented as group "Z" in the drawing) and thus the selective "capture" of the oligonucleotide by the capture support. This capture allows all impurities and any other unreactive oligonucleotides in the solution, for example failure sequences, to be washed away from the capture support. After removal of the impurities and non-reactive oligonucleotides, the purified, full-length oligonucleotide can be dissociated from the capture support, either by a "soft release", where the covalent linker adduct "Z" is cleaved to regenerate the original "X" and "Y" groups, or by a "hard release", where the covalent linker adduct "Z" is cleaved from the 5'-end of the purified oligonucleotide. Where the oligonucleotide is cleaved from the capture support by a soft release, the X group can be removed in a subsequent step. For example, where the X group comprises a trityl group modified with an electron-withdrawing moiety, this group can be removed by a mild aqueous acid treatment, with or without catalyst, thus minimizing the possibility of depurinations or any other detrimental reaction of the oligonucleotide. Furthermore, this method also allows for additional covalent reactions involving the linker-modified group X on the oligonucleotide, and/or regeneration of the capture support "Y" functional group for reuse of the solid phase support in one step. Details of the methods and reagents traditionally used for cleavage and deprotection of synthetic oligonucleotides are also well known in the art. See, e.g., Andrews et al. (2021) *J. Org. Chem.* 86 49-61.

Figure 1B:
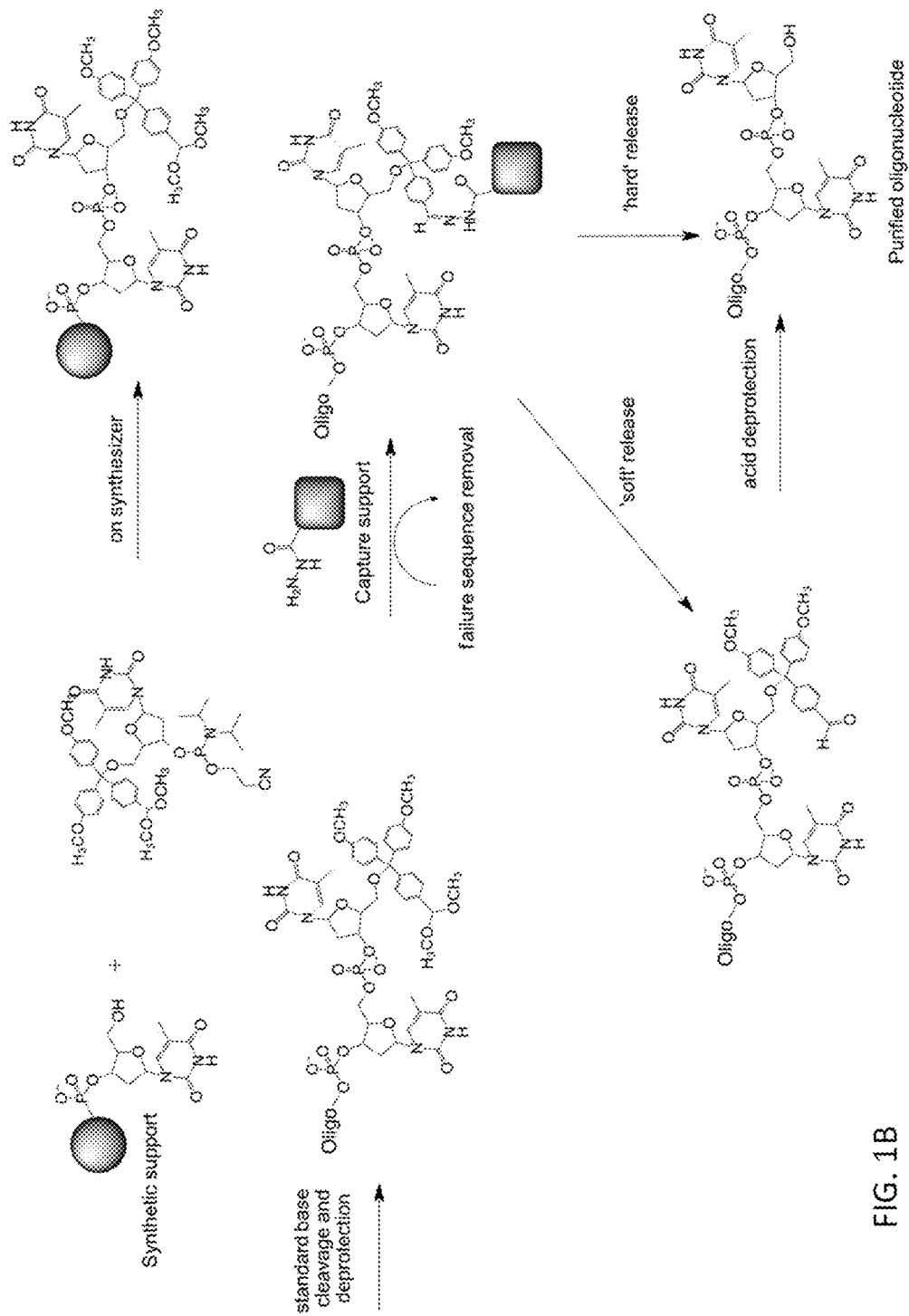
FIG. 1B illustrates an exemplary specific scheme for the synthesis of a synthetic oligonucleotide comprising a 5'-O-4-formyl-DMT dimethyl acetal linker moiety, standard cleavage from the synthetic support and deprotection of the nucleobases, and purification of the oligonucleotide by capture and release using a hydrazide-modified capture support.

FIG. 1B shows a more specific exemplary scheme for the synthesis and purification of a synthetic oligonucleotide employing a 5'-O-4-formyl DMT (4FB-DMT) linker moiety, which is derivatized as a dimethyl acetal. The method includes standard cleavage of the oligonucleotide from the synthetic support and deprotection of the nucleobases, and purification of the oligonucleotide by capture and release using a hydrazide-modified capture support.

The modified synthetic biopolymeric compounds described above, which may also be referred to as reactive, or selectively-reactive, synthetic biopolymeric compounds, thus typically comprise a trityl group (i.e., a triphenylmethyl group) that has been modified either with a carbonyl moiety, an amino moiety, a component of a click reaction, or a derivative of any of these moieties, as will be described in further detail in the following section.

Selectively-Reactive Linker Moieties

As just described, the reactive synthetic biopolymeric compounds of the instant disclosure, and the reagent compounds used to synthesize these biopolymeric compounds, comprise a selectively-reactive linker moiety that facilitates capture of the reactive synthetic biopolymeric compound by a complementary selectively-reactive linker moiety on a capture support. Although a variety of selectively-reactive linker moiety pairs can be usefully employed in the instant reagent compounds, reactive biopolymeric compounds, capture supports, and the associated methods of preparation and use, the moieties are preferably chosen so that they selectively react with one another as efficiently and specifically as possible, in order to form a covalent linkage, and in some cases a reversibly-cleavable covalent linkage.

Examples of reversibly-cleavable covalent linkages usefully formed by the selectively-reactive linker moiety pairs of the instant disclosure include hydrazones, oximes, and other suitable Schiff base moieties. The reactions between the selectively-reactive linker moiety pairs are preferably complete, or nearly complete, at low molar concentrations of reactants in aqueous solution, and with rapid reaction kinetics. Specifically, in some embodiments, a first selectively-reactive linker moiety can comprise a reactive carbonyl group, or a derivative thereof, and the complementary second selectively-reactive linker moiety can comprise a reactive amino group, or a derivative thereof. Alternatively, the first selectively-reactive linker moiety can comprise a reactive amino group, or a derivative thereof, and the complementary second selectively-reactive linker moiety can comprise a reactive carbonyl group, or a derivative thereof.

In preferred embodiments, the reactive carbonyl group of the first or second selectively-reactive linker moiety is an aliphatic or aromatic aldehyde or ketone, or a derivative thereof, and the reactive amino group of a complementary first or second selectively-reactive linker moiety is an aliphatic or aromatic hydrazide, an aliphatic or aromatic hydrazine, an aliphatic or aromatic hydroxylamine, or a derivative thereof. Non-limiting examples of such selectively-reactive linker moieties can be found, for example, in U.S. Pat. No. 7,102,024, which is incorporated by reference herein in its entirety for all purposes.

For example, hydrazone conjugation moieties can be formed by the reaction of a hydrazino group, or a protected hydrazino group, with a carbonyl moiety. Exemplary hydrazino groups include aliphatic, aromatic, or heteroaromatic hydrazine, semicarbazide, carbazide, hydrazide, thiosemicarbazide, thiocarbazide, carbonic acid dihydrazine, or hydrazine carboxylate groups, as illustrated in the following structures:

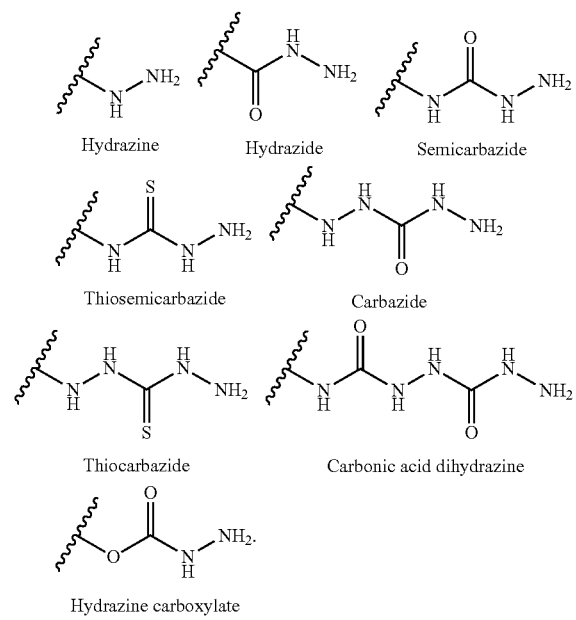

Hydrazine    Hydrazide    Semicarbazide

Thiosemicarbazide    Carbazide

Thiocarbazide    Carbonic acid dihydrazine

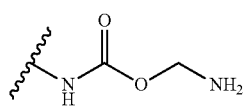

Hydrazine carboxylate

Oxime conjugation moieties can be formed by the reaction of an oxyamino group, or a protected oxyamino group, with a suitable carbonyl moiety, including any of the above-mentioned carbonyl groups or their derivatives. An exemplary oxyamino group has the following structure:

The hydrazino and oxyamino groups can be protected by formation of a salt of the hydrazino or oxyamino group, including but not limited to, mineral acid salts, such as but not limited to hydrochlorides and sulfates, and salts of organic acids, such as but not limited to acetates, haloacetates, lactates, malates, tartrates, citrates, ascorbates, succinates, butyrates, valerates and fumarates, or any amino or hydrazino protecting group known to those of skill in the art (see, e.g., Greene et al. (1999) Protective Groups in Organic Synthesis ($3^{rd}$ Ed.) (J. Wiley Sons, Inc.)).

In preferred embodiments of the instant disclosure, a reversibly covalent linkage is formed by the reaction of an oxyamino-containing component and an aromatic aldehyde-containing component in the presence of an aniline catalyst (see, e.g., Dirksen et al. (2006) Angew. Chem. 45:7581-7584 (DOI: 10.1002/anie.200602877).

Specific hydrazino labeling reagents, labeling methods, and uses of the labeled products are disclosed in PCT International Publication Nos. WO 01/70685 A2; WO 02/10431 A2; WO 02/10432 A2; WO 02/57422 A2; WO 2008/140452 A1; WO 2011/100493 A1; WO 2012/071428 A2; WO 2013/177046 A1; WO 2016/127149 A2; and WO 2018/017606 A1; and U.S. Patent Application Publication No. 2008/0221343 A1, each of which is incorporated by reference herein in its entirety for all purposes.

As mentioned above, in some embodiments, the selectively-reactive linker moiety used in the instant C&R technology is a component of a "click" reaction, for example the copper-catalyzed reaction of an azide-substituted component with an alkyne-substituted component to form a triazole conjugation moiety. See Kolb et al. (2001) Angew. Chem. Int. Ed. Engl. 40:2004; Evans (2007) Aus. J. Chem. 60:384. Copper-free variants of this reaction, for example the strain-promoted azide-alkyne click reaction, may also be used to form the high-efficiency conjugation moiety. See, e.g., Baskin et al. (2007) Proc. Nat Acad. Sci. U.S.A. 104:16793-97. Other click reaction variants include the reaction of a tetrazine-substituted component with either an isonitrile-substituted component (Stöckmann et al. (2011) Org. Biomol. Chem. 9:7303) or a strained alkene-substituted component (Karver et al. (2011) Bioconjugate Chem. 22:2263).

The basic features of a click reaction are well understood by those of ordinary skill in the art. See Kolb et al. (2001) Angew. Chem. Int. Ed. Engl. 40:2004. Useful click reactions include generally but are not limited to [3+2]cycloadditions, such as the Huisgen 1,3-dipolar cycloaddition, and in particular the Cu(I)-catalyzed stepwise variant, thiol-ene click reactions, Diels-Alder reactions and inverse electron demand Diels-Alder reactions, [4+1] cycloadditions between isonitriles (isocyanides) and tetrazines, nucleophilic substitutions, especially to small strained rings like epoxy and aziridine compounds, carbonyl-chemistry-like formation of ureas, and some addition reactions to carbon-carbon double bonds. Any of the above reactions may be used without limitation to prepare complementary selectively-reactive linker moieties for use in the instant C&R technologies.

The above-described selectively-reactive linker moieties (e.g., a reactive carbonyl group, a reactive hydrazino group, a reactive oxyamino group, a component of a click reaction, or their derivatives) can be incorporated into the reagent compounds and reactive synthetic biopolymeric compounds of the disclosure, for example as described herein. Complementary selectively-reactive linker moieties can likewise be incorporated into suitable solid supports using appropriate chemical linkers, and the modified capture supports can be used in methods of purifying reactive synthetic biopolymeric compounds, for example as described herein. Hydrazine-based and carbonyl-based bifunctional crosslinking reagents for use in the conjugation and immobilization of biomolecules are described in U.S. Pat. No. 6,800,728. The use of high-efficiency bisaryl-hydrazone linkers to form oligonucleotide conjugates in various detection assays and other applications is described in PCT International Publication No. WO 2012/071428. Each of the above references is hereby incorporated by reference herein in its entirety for all purposes.

Reagent Compounds for Oligonucleotide Synthesis and Purification

In one aspect, the disclosure provides reagent compounds that can, for example, be used in the preparation of reactive oligonucleotides for use in the capture and release techniques described herein. The reagent compounds can, for example, have the following structure:

T'-C'P' wherein T' is a modified trityl protecting group, C' is a connecting moiety, and P' is a phosphoramidite or phosphoramidate.

The modified trityl protecting group in these reagent compounds preferably has the following general structure:

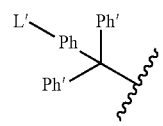

wherein L' comprises any of the above-described selectively-reactive linker moieties, Ph is an optionally substituted phenylene, and each Ph' is independently an optionally substituted phenyl group. The optional substituents of the phenylene and phenyl groups can be, for example, one or more electron-withdrawing groups, which can modulate the deprotection conditions required for release of the trityl protecting group from a synthetic biopolymer modified with this protecting group. The optional substituents can, in some embodiments, be one or more $C_1$-$C_4$ alkoxy groups, one or more $C_1$-$C_4$ alkyl groups, or any combination of these substituents.

In some embodiments, the reagent compounds can have the following structure:

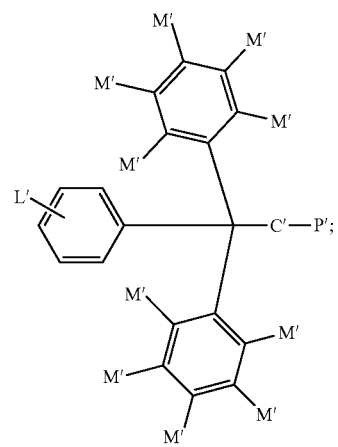

wherein L' comprises any of the above-described selectively-reactive linker moieties, each M' is independently a $C_1$-$C_4$ alkoxy group, a $C_1$-$C_4$ alkyl group, a hydrogen, or a combination of these groups, C' is a connecting moiety, and P' is a phosphoramidite or phosphoramidate.

In more specific embodiments, the reagent compounds can have the following structure:

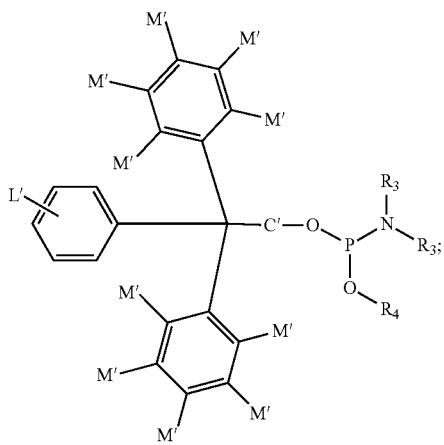

wherein each $R_3$ is independently a $C_1$-$C_6$ alkyl group, and $R_4$ is an optionally-substituted $C_1$-$C_6$ alkyl group or a saccharide-substituted polyethylene glycol group, for example as described in U.S. Pat. Nos. 10,087,208 and 10,669,301. More specifically, $R_4$ is a cyano-substituted $C_1$-$C_6$ alkyl group.

In even more specific embodiments, the reagent compounds can have the following structure:

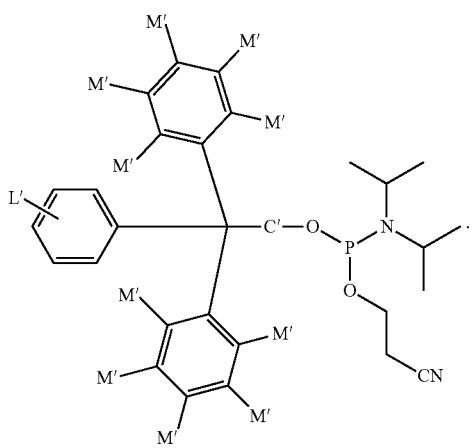

In specific embodiments of these reagent compounds, at least one M' can be a methoxy group. For example, the reagent compounds can have the structure:

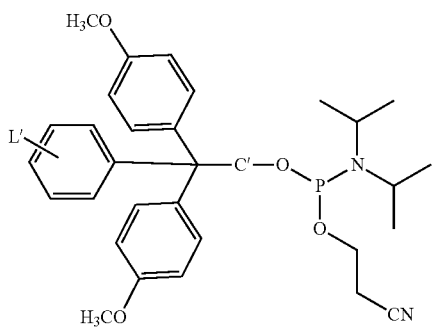

or can even have the structure:

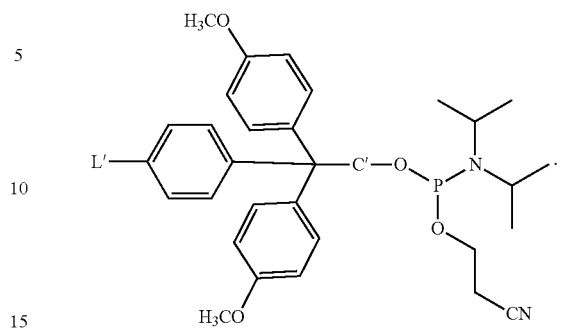

In some embodiments, the reagent compounds have the following structure:

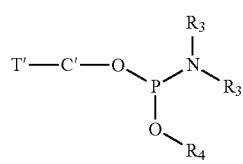

wherein T' is a modified trityl protecting group, C' is a connecting moiety, each $R_3$ is independently a $C_1$-$C_6$ alkyl group, and $R_4$ is an optionally-substituted $C_1$-$C_6$ alkyl group or a saccharide-substituted polyethylene glycol group. More specifically, $R_4$ is a cyano-substituted $C_1$-$C_6$ alkyl group.

In other specific embodiments, the reagent compounds can have the following structure:

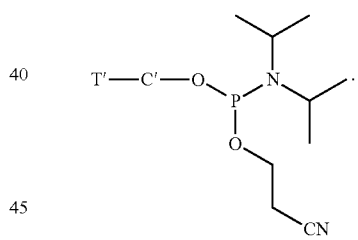

In some embodiments, the reagent compounds have the following structure:

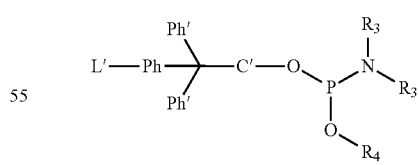

wherein L' comprises any of the above-described selectively-reactive linker moieties, Ph is an optionally substituted phenylene, each Ph' is independently an optionally substituted phenyl group, C' is a connecting moiety, each $R_3$ is independently a $C_1$-$C_6$ alkyl group, and $R_4$ is an optionally-substituted $C_1$-$C_6$ alkyl group or a saccharide-substituted polyethylene glycol group. More specifically, $R_4$ is a cyano-substituted $C_1$-$C_6$ alkyl group.

In other specific embodiments, the reagent compounds can have the following structure:

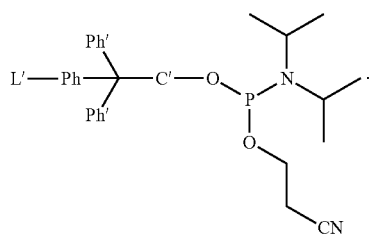

The connecting moiety, C', of the above-described reagent compounds is chosen in view of the intended use of the oligonucleotide being prepared using the reagent compound. For routine oligonucleotide synthesis, where the product of the solid-phase synthesis is to be purified using the capture and release techniques described herein, the connecting moiety of any of the above reagent compound structures can be a natural nucleoside residue or a modified nucleoside residue, such as a 2'-O-methoxyethyl (MOE) nucleoside residue, a 2',4'-constrained MOE (cMOE) nucleoside residue, a 2',4'-constrained ethyl (cEt) nucleoside residue, or a locked nucleic acid (LNA) nucleoside residue.

Reagent compounds comprising any of these nucleoside residues as the connecting moiety correspond generally to traditional nucleoside phosphoramidite reagent compounds, for example the reagent compounds that were originally described by Beaucage and Caruthers (*Tet. Lett.* 22:1859 (1981)), but with a selectively-reactive linker moiety on their 5' protecting group, for example on a modified trityl protecting group. Such reagent compounds can accordingly be reacted with the 5'-OH of a synthetic oligonucleotide on a solid support, preferably during the last step of a standard solid-phase oligonucleotide synthesis reaction. See, e.g., Ellington et al. (2000) Introduction to the Synthesis and Purification of Oligonucleotides in *Current Protocols in Nucleic Acid Chemistry* A.3C.1-A.3C.22, which is incorporated herein by reference in its entirety for all purposes.

Reagent compounds with a nucleoside residue or a locked nucleoside residue as the connecting structure can accordingly have the structure:

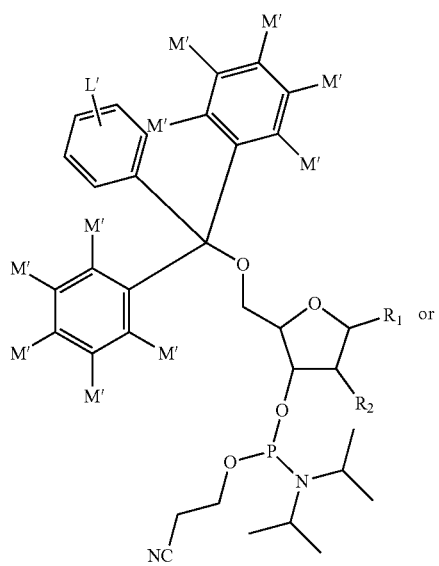

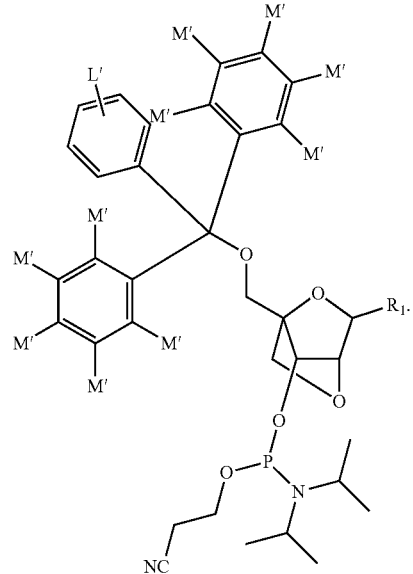

They can more specifically have the structure:

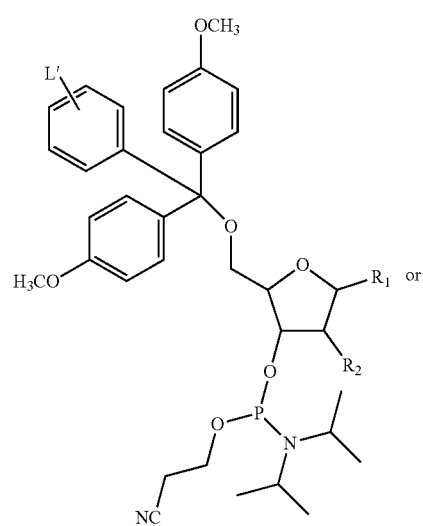

-continued

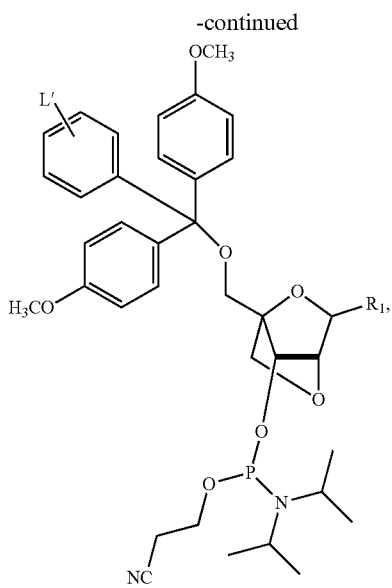

and can even more specifically have the structure:

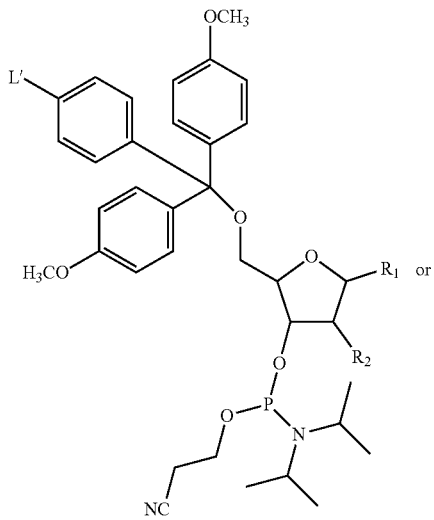

-continued

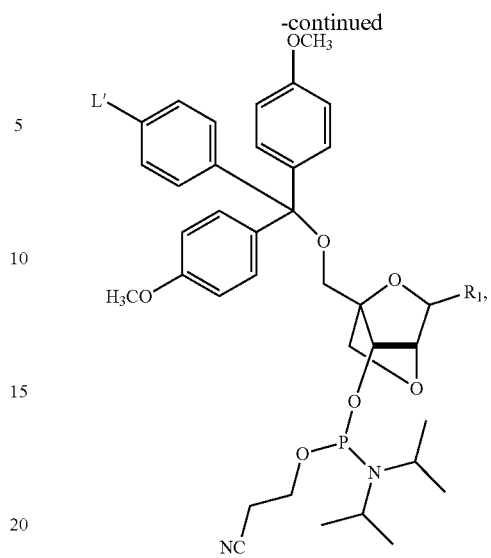

where L' and each M' is as defined above.

In these structures, $R_1$ is —H, a nucleobase, a protected nucleobase, or a modified nucleobase, and $R_2$ is —H, -hydroxyl, protected -hydroxyl, modified -hydroxyl, such as a methoxy, a methoxyethyl, an ester, a thionoester, a carbamate, or a thiocarbamate, or -halo. More specifically, $R_2$ can be —H, -hydroxyl, protected -hydroxyl, —OCH$_3$,

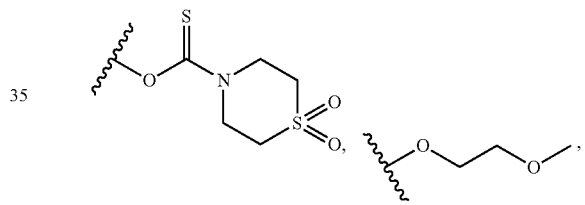

or -fluoro. As is known in the art, modification of the 2'-position of the ribose group in a synthetic oligonucleotide can confer nuclease resistance and other advantageous properties to the oligonucleotide.

In some reagent compound embodiments, the connecting moiety comprises a morpholino nucleoside residue. These reagent compounds can be used to synthesize morpholino oligonucleotides, as will be described in more detail below. Exemplary reagent compounds comprising such morpholino moieties include the following structures:

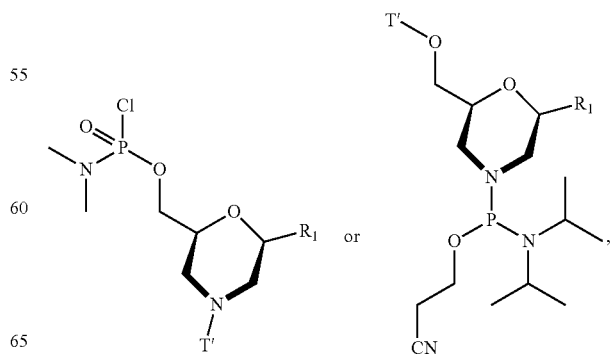

wherein the $R_1$ group is —H, a nucleobase, a protected nucleobase, or a modified nucleobase, and the T' group is any of the above-defined modified trityl protecting groups.

In some embodiments, the reagent compounds can have the following structures:

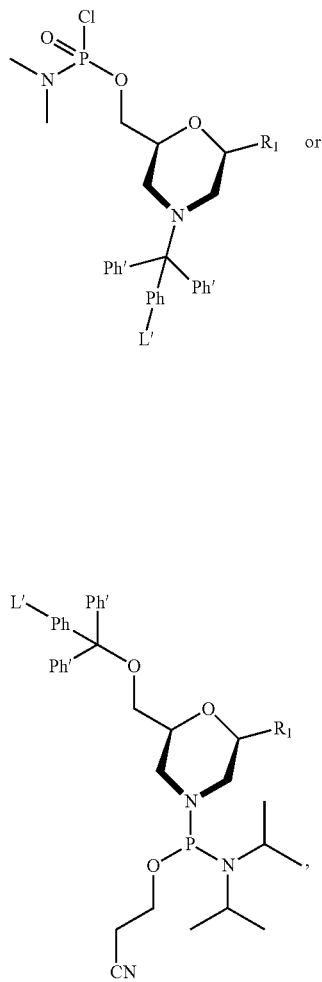

wherein the $R_1$ group is —H, a nucleobase, a protected nucleobase, or a modified nucleobase, L' comprises any of the above-described selectively-reactive linker moieties, Ph is an optionally substituted phenylene, and each Ph' is independently an optionally substituted phenyl group.

More specifically, the reagent compounds can have the following structures:

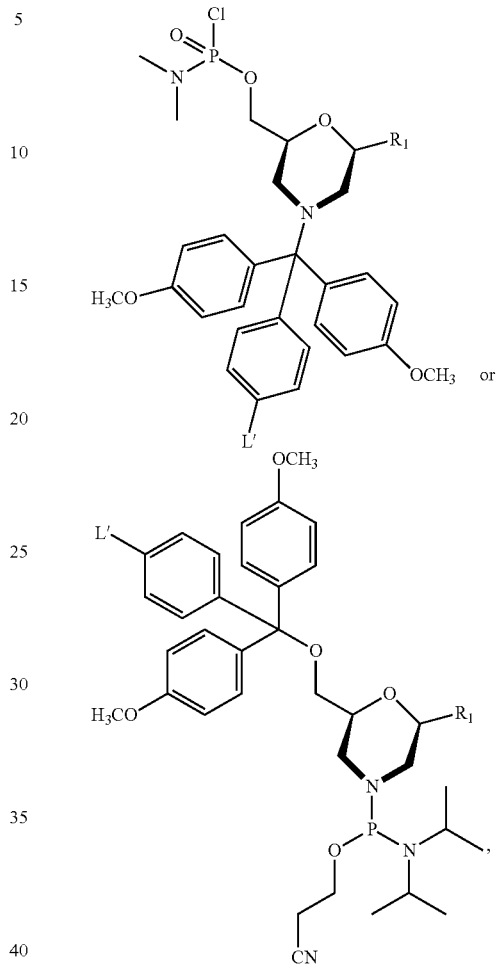

wherein the $R_1$ group is —H, a nucleobase, a protected nucleobase, or a modified nucleobase, and L' comprises any of the above-described selectively-reactive linker moieties.

Biopolymeric compounds can be prepared from these reagent compounds using either phosphoramidite P(III) or phosphoramidate P(V) chemistry to generate phosphorodiamidate morpholino oligonucleotides, thiophosphoramidate morpholino oligonucleotides, or phosphoramidate morpholino oligonucleotides. See, e.g., Paul, S.; Caruthers, M. H. (2023) *Molecules*, 28, 5380. The different reagent compounds modify either the 3' or the 5' end of the biopolymeric compound, as is understood by those of ordinary skill in the art.

The nucleobase used in any of the above reagent compounds is preferably a protected nucleobase. The specific nucleobase used in a particular reagent compound will depend on the desired nucleotide sequence of the oligonucleotide being synthesized, as is understood by those of ordinary skill in the art. For a 2'-deoxyribonucleoside reagent compound, the nucleobases used most commonly are thymine, adenine, cytosine, and guanine, or protected versions of these bases, such as Bz-dA, Bz-dC, and iBu-dG, or nucleobases containing "mild deprotection" protecting groups such as phenoxyacetyl (Pac), 4-isopropyl-phenoxyacetyl (iPr-Pac), or acetyl groups, but any suitable nucleobase, or protected nucleobase, including a natural or unnatural nucleobase, or a modified nucleobase, can be used in the instant reagent compounds. For a ribonucleoside reagent compound, or a 2'-protected or modified version of such compounds, the nucleobases used most commonly are uracil, adenine, cytosine, and guanine, or protected versions of these bases, but any suitable nucleobase, or protected nucleobase, can be used in the instant reagent compounds. Modified uracil nucleobases including, but not limited to, pseudouracil, N'-methylpseudouracil, and 5-methoxyuracil can also be used. See, e.g., Ellington et al. (2000) Introduction to the Synthesis and Purification of Oligonucleotides in *Current Protocols in Nucleic Acid Chemistry* A.3C.1-A.3C.22.

Other exemplary nucleobases useful in the instant reagent compounds include hypoxanthine, xanthine, 7-methylguanine, 5,6-dihydrouracil, 5-methylcytosine, and 5-hydroxymethylcytosine, or protected versions of these nucleobases. Nucleobases that can be deprotected under mild conditions include those modified with N-benzoyl (Bz), N-acetyl (Ac), N-isobutyryl (iBu), N-phenoxyacetyl (PAC), N-tert-butylphenoxyacetyl (tBPAC), N-dimethylformamidine (DMF), and N-p-isopropyl-phenoxyacetyl (iPrPAC) groups.

It should be understood that the term "residue" refers to the residual portion of a molecule that has been incorporated into the structure of a larger molecule. For example, the reagent compounds illustrated above with a nucleoside residue or a locked nucleoside residue do not include the hydrogens that would normally be present on the 3' and 5' hydroxyl groups of the corresponding ribonucleoside. Likewise, the linker residues described below do not include terminal hydrogen atoms but instead include only the bonds that connect the linker structure to the rest of the reagent compound.

It should also be understood that the selectively-reactive linker moiety in these compounds can be any of the above-described selectively-reactive linker moieties. More specifically, the selectively-reactive linker moiety can comprise a reactive carbonyl group, a reactive amino group, a component of a click reaction, or a derivative of any of these groups. The specific choice of selectively-reactive linker moiety will depend on the counterpart selectively-reactive linker moiety that is associated with the capture support to be used in the capture and release process, as would be understood by those of ordinary skill in the art upon review and understanding of the instant disclosure.

Two exemplary phosphoramidite reagent compounds comprising a nucleoside residue as the connecting moiety are illustrated below:

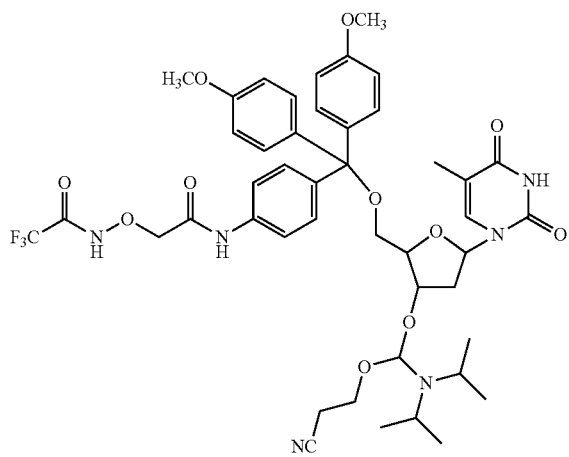

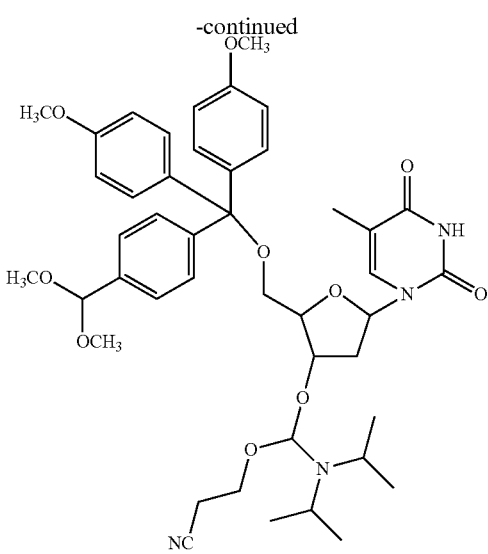

The compound on the left comprises a 5'-DMT modified dT-phosphoramidite with a selectively-reactive linker moiety comprising an oxyamino group derivatized with a trifluoroacetyl protecting group, and the compound on the right comprises a 5'-DMT modified dT phosphoramidite with a selectively-reactive linker moiety comprising a formyl group derivatized as a dimethyl acetal.

Reagent compounds of the instant disclosure can additionally be used to incorporate linker moieties, polyethylene glycol (PEG) chains, and other chemical agents with a variety of desired functionalities, onto the terminus of a synthetic oligonucleotide. For example, to enable ligation of purified oligonucleotides during site-directed mutagenesis, to clone PCR products into vectors, to create sgRNA for use in CRISPR (clustered regularly interspaced short palindromic repeats) gene editing, and for other types of related genetic manipulations, it may be advantageous to prepare reagent compounds that provide for the incorporation of a phosphate group at the 5'-terminus of a synthetic oligonucleotide. The incorporation of a phosphate group, PEG chain, or another linker moiety attached to the end of an oligonucleotide using a reagent compound of the instant disclosure, and the purification of an oligonucleotide comprising such groups can be confirmed by LC-MS. A purified, 5'-phosphate-terminated oligonucleotide can subsequently be ligated to the 3'-OH terminus of a second oligonucleotide or other suitably-reactive molecule.

Synthetic, linker-terminated oligonucleotides and other linker-terminated biopolymeric compounds can be used for many additional purposes. Such alternative reagents greatly expand the technical and commercial utility of the capture-and-release technology described herein beyond just the preparation and purification of traditional unmodified synthetic oligonucleotides. Such alternative functionalized moieties include, but are not limited to, amino, thiol, aminooxy, or azido groups for conjugation to various biomolecules and/or surfaces after purification of the linker-containing oligonucleotide incorporating the capture and release technology. Additionally, detection moieties, such as, for example, fluorophores, may be incorporated onto the terminus of a synthetic oligonucleotide, or other suitable biopolymeric compound, using the above reagent technology.

In order to implement these novel embodiments of the reagent compounds, the disclosure therefore additionally provides reagent compounds wherein the connecting moiety, C', in the above structures comprises a linker residue. More specifically, the linker residue of these compounds can, for example, in some embodiments comprise an optionally substituted —$C_{1-8}$-alkanediyl-, wherein each carbon atom is optionally replaced with an optionally substituted heteroatom.

In some embodiments of these compounds, the linker residue can comprise:

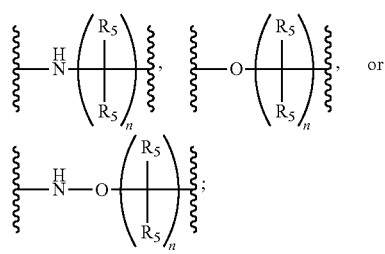

wherein n is 1-6 and each $R_5$ is independently —H, $C_{1-3}$-alkyl, $C_{1-3}$-carboxylate, $C_{1-3}$-alkyl-$C_{1-3}$-carboxylate, $C_{1-3}$-alkoxy, -halo, -nitro, -amino, -amido, or -hydroxyl.

In more specific embodiments, the linker residue can comprise:

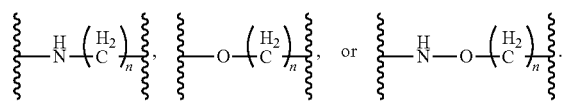

In even more specific embodiments, the linker residue can comprise:

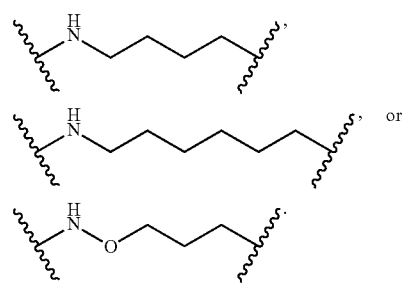

In other even more specific embodiments, the linker residue can comprise:

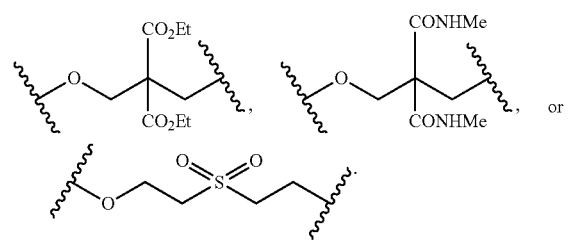

Exemplary phosphoramidite reagent compounds comprising a linker residue as the connecting moiety are illustrated below, where the L' group comprises any of the above-described selectively-reactive linker moieties. The bottom three structures can be used to incorporate a phosphate group on the 5'-terminus of a synthetic oligonucleotide, as is understood by those of ordinary skill in the art. See, e.g., Horn et al. (1986) *Tetrahedron Lett.*, 27, 4705-4708.

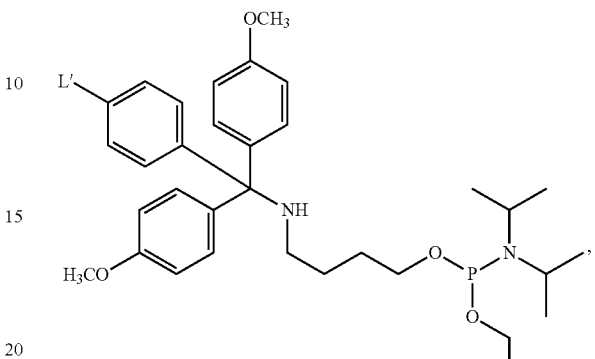

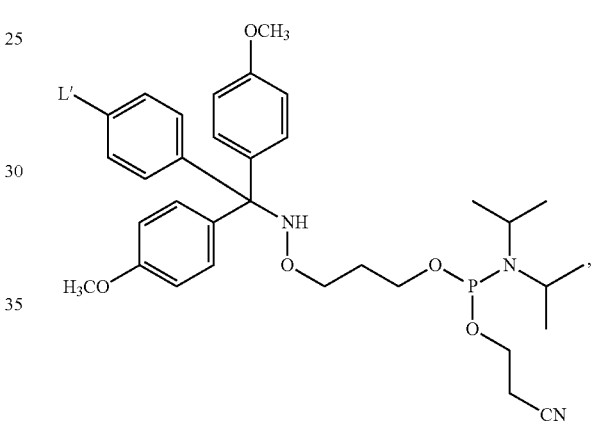

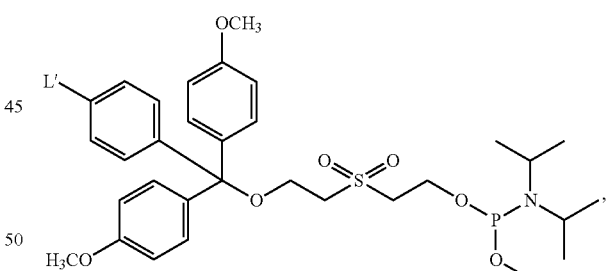

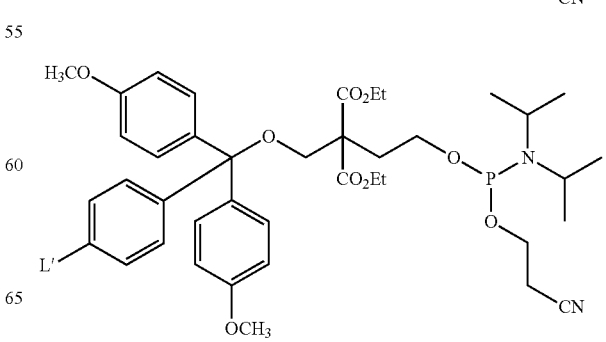

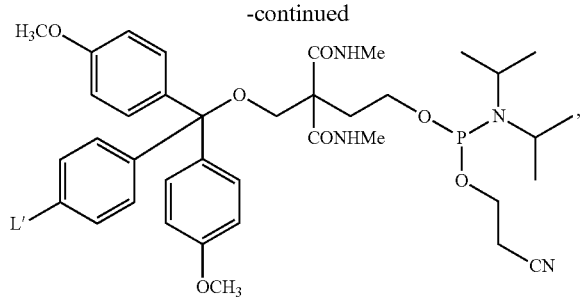

Other useful reagents employing the instant strategies include PEG groups and spacers. For example, several FDA approved nucleic acid therapeutics contain a PEG-alcohol at their 5'-termini, which is critical to reduce exonuclease degradation and to increase drug solubility. Such modified oligonucleotides can be prepared and purified using any of the above-described reagent compounds wherein the connecting moiety comprises a polyethylene glycol (PEG) residue. In these embodiments, the connecting moiety can, for example, comprise the structure:

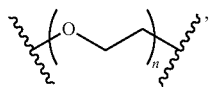

wherein n is from 1 to 20, from 1 to 40, from 1 to 60, from 1 to 80, from 1 to 100, or from 1 to 200 or higher. In other embodiments, the polyethylene glycol is a branched polyethylene glycol residue.

An exemplary phosphoramidite reagent compound comprising a polyethylene glycol as the connecting moiety has the following structure:

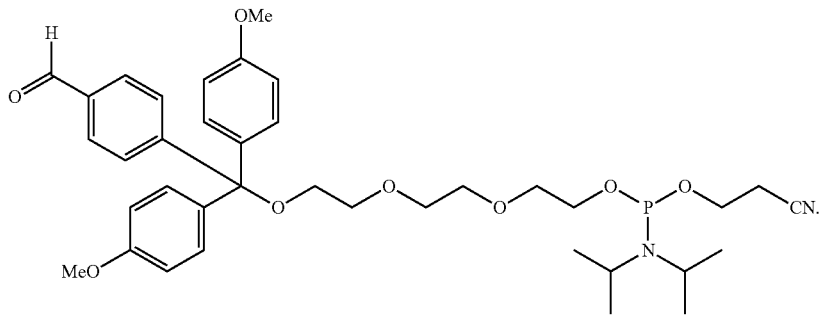 [SMILES: COc1ccc(C(OCCOCCOCCOP(OCCC#N)N(C(C)C)C(C)C)(c2ccc(C=O)cc2)c2ccc(OC)cc2)cc1]

Reactive Biopolymeric Compounds

In another aspect are provided reactive biopolymeric compounds that can, for example, be purified according to the capture and release techniques described herein. The reactive biopolymeric compounds preferably comprise a first terminal residue that is coupled to a modified trityl protecting group comprising a selectively-reactive linker moiety. More specifically, the first terminal residue is coupled to any of the modified trityl protecting groups described above.

In some embodiments, the reactive biopolymeric compound of the disclosure has the structure:

T'-BP' wherein T' is a modified trityl protecting group and BP' is a biopolymer.

The biopolymer, BP', of these structures can be any suitable biopolymer, whether natural, modified, or unnatural. The biopolymer is preferably a synthetic biopolymer that is prepared by the stepwise addition of reactive monomeric units to a solid support. Incomplete biopolymeric structures can be capped during the synthetic process to prevent them from being further extended and ultimately derivatized by the modified trityl protecting group, as is understood by those of ordinary skill in the art.

In some embodiments, the synthetic biopolymer is a synthetic oligonucleotide. In some embodiments, the synthetic biopolymer is a synthetic polypeptide. In some embodiments, the synthetic biopolymer is a synthetic oligosaccharide. In some embodiments, the synthetic biopolymer is a combination of any of the above biopolymers.

In some embodiments, the biopolymer is a modified biopolymer, for example, a modified oligonucleotide, a modified polypeptide, or a modified oligosaccharide, in any combination.

In some embodiments, the biopolymer is an unnatural analogue of a natural biopolymer. For example, in some embodiments, the biopolymer is a morpholino oligonucleotide, for example a phosphorodiamidate morpholino oligonucleotide (PMO), a thiophosphoramidate morpholino oligonucleotide (TMO), or a phosphoramidate morpholino oligonucleotide (MO). These unnatural biopolymers have a unique structure that includes a morpholine ring and a phosphorodiamidate, thiophosphoramidate, or phosphoramidate linkage instead of the 2'-deoxy-ribose-phosphate or ribose-phosphate backbone found in natural DNA and RNA, respectively. Phosphorodiamidate morpholino oligonucleotides are typically synthesized with phosphoramidate P(V) chemistry on a solid support using chlorophosphoramidate morpholino nucleosides in the 5' to 3' direction, although alternative synthetic strategies using phosphoramidite P(III) chemistry are available. See, e.g., Paul, S.; Caruthers, M. H. (2023) *Molecules*, 28, 5380. Morpholino nucleosides are typically protected with a trityl group on the 3' amino group of the morpholine ring. This group can be substituted with a modified trityl protecting group comprising a selectively-reactive linker moiety of the instant disclosure for use in the capture and release compounds and methods disclosed herein, as would be understood by those of ordinary skill in the art. Similarly, the 6' hydroxyl group of the morpholino nucleoside can be protected with a modified trityl protecting group comprising a selectively-reactive linker moiety of the instant disclosure for use in the instant capture and release compounds and methods. Biopolymeric compounds with morpholino nucleosides comprising a selectively-reactive linker group can be synthesized, for example, using the morpholino reagent compounds described above.

The modified trityl protecting group, T', of the reactive biopolymeric compounds can be any of the modified trityl protecting groups used in the above-described reagent compounds for oligonucleotide synthesis. In some embodiments, the modified trityl group can be a modified dimethoxytrityl group. For example, the modified dimethoxytrityl group can comprise a reactive aldehyde group, a reactive oxyamino group, a reactive hydrazino group, a component of a click reaction, or a derivative of any thereof.

In some embodiments, the modified trityl protecting group of the reactive biopolymeric compounds has the following structure:

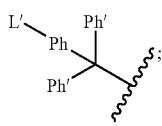

wherein L' comprises any of the above-described selectively-reactive linker moieties, Ph is an optionally substituted phenylene moiety, and each Ph' is independently an optionally substituted phenyl group. The optional substituents of the phenylene and phenyl groups can be, for example, one or more electron-withdrawing groups, which can modulate the deprotection conditions required for release of the trityl group from the synthetic biopolymer. The optional substituents can, in some embodiments, be one or more $C_1$-$C_4$ alkoxy groups, one or more $C_1$-$C_4$ alkyl groups, or any combination of these substituents.

In some embodiments, the modified trityl protecting group of the reactive biopolymeric compound has the following structure:

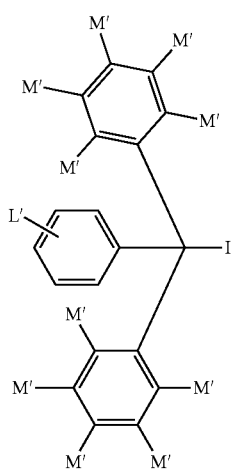

wherein L' comprises the selectively-reactive linker moiety, and each M' is independently a $C_1$-$C_4$ alkoxy group, a $C_1$-$C_4$ alkyl group, a —H, or a combination of any of these groups.

In more specific embodiments, the modified trityl protecting group of the reactive biopolymeric compound comprises the structure:

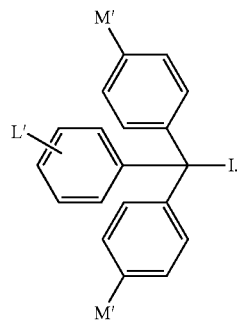

Even more specifically, the reactive biopolymeric compound comprises the structure:

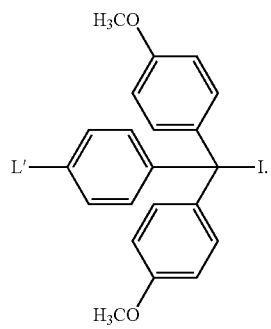

In some embodiments, the reactive biopolymeric compounds of the disclosure comprise a selectively-reactive linker moiety that comprises a reactive carbonyl group capable of forming a hydrazone or oxime linkage, or a derivative thereof. Even more specifically, the carbonyl group can be an aldehyde, or a derivative of an aldehyde.

In some embodiments, the reactive biopolymeric compounds of the disclosure comprise a selectively-reactive linker moiety that comprises a reactive oxyamino group, a reactive hydrazino group, a component of a click reaction, or a derivative of any thereof.

In some embodiments, the reactive biopolymeric compounds of the disclosure comprise the structure:

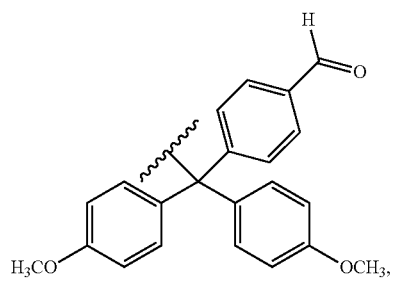

-continued

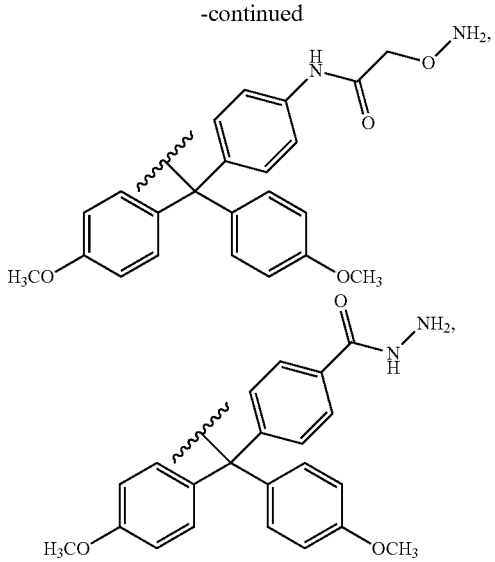

or a derivative thereof.

The modified trityl protecting group of the above reactive biopolymeric compounds can be attached to the biopolymer using any suitable chemistry. In preferred embodiments, the modified trityl protecting group is attached to the synthetic biopolymer in the last step of the synthetic process using a monomeric unit that includes the modified trityl protecting group. For example, where the synthetic biopolymer is a synthetic oligonucleotide that is prepared by addition of monomeric nucleoside residues to the 5' terminus of an oligonucleotide attached to a solid synthetic support, the monomeric unit can be any of the reagent compounds for oligonucleotide synthesis described above, where the reagent compounds comprise a phosphoramidite.

In some embodiments, the modified trityl group does not comprise an N-hydroxy-succinimidyl group.

In some embodiments, a terminal residue of the reactive biopolymeric compound remains attached to a solid support, for example to a solid synthetic support.

Methods of synthesizing reactive biopolymeric compounds comprising the above-described modified trityl protecting groups are described below.

Reagent Compounds Comprising a Reactive Modified Trityl Protecting Group

In another aspect are provided reagent compounds comprising a reactive modified trityl protecting group that can be used, for example, to attach the modified trityl protecting group to a biopolymer, or other reactive compound of interest, in order to facilitate the purification of that compound according to the capture and release techniques described herein. The reagent compounds preferably comprise a modified trityl protecting group comprising a selectively-reactive linker moiety. More specifically, the reagent compounds comprise a modified trityl protecting group attached to a suitable leaving group, so that the compounds can be used to label a reactive compound of interest at a reactive residue, typically a nucleophilic residue, as would be understood by those of ordinary skill in the chemical arts.

In some embodiments, the reagent compound of the disclosure has the structure:

T'-X wherein T' is a modified trityl protecting group, and X is a leaving group.

The X of these structures can be any suitable leaving group, and is preferably a leaving group that yields an anionic product after the reagent compound has reacted with a target compound. In some embodiments, X is a halo group, more specifically, a fluoro or chloro group. In some embodiments, X is an acyl leaving group, for example, an acetyl or a trihaloacetyl leaving group. More specifically, the leaving group is a trifluoroacetyl leaving group.

The modified trityl protecting group, T', of the reagent compounds can be any of the modified trityl protecting groups used in the above-described reagent compounds for oligonucleotide synthesis. In some embodiments, the modified trityl group can be a modified dimethoxytrityl group. For example, the modified dimethoxytrityl group can comprise a reactive aldehyde group, a reactive oxyamino group, a reactive hydrazino group, a component of a click reaction, or a derivative of any thereof.

In some embodiments, the modified trityl protecting group of the reagent compounds has the following structure:

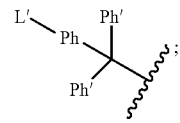

wherein L' comprises any of the above-described selectively-reactive linker moieties, Ph is an optionally substituted phenylene moiety, and each Ph' is independently an optionally substituted phenyl group. The optional substituents of the phenylene and phenyl groups can be, for example, one or more electron-withdrawing groups, which can modulate the stability and reactivity of the trityl cation. The optional substituents can, in some embodiments, be one or more $C_1$-$C_4$ alkoxy groups, one or more $C_1$-$C_4$ alkyl groups, or any combination of these substituents.

In some embodiments, the modified trityl protecting group of the reagent compounds has the following structure:

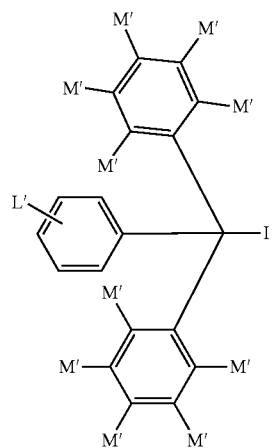

wherein L' comprises the selectively-reactive linker moiety, and each M' is independently a $C_1$-$C_4$ alkoxy group, a $C_1$-$C_4$ alkyl group, a —H, or a combination of any of these groups.

In more specific embodiments, the modified trityl protecting group of the reagent compounds has the structure:

Even more specifically, the modified trityl protecting group has the structure:

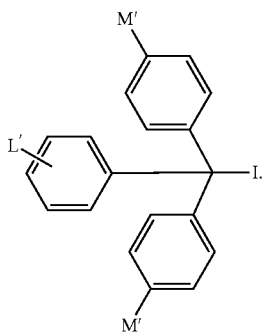

In some embodiments, the selectively-reactive linker moiety of the modified trityl protecting group comprises a reactive carbonyl group capable of forming a hydrazone or oxime linkage, or a derivative thereof. Even more specifically, the carbonyl group can be an aldehyde, or a derivative of an aldehyde.

In some embodiments, the selectively-reactive linker moiety of the modified trityl protecting group comprises a reactive oxyamino group, a reactive hydrazino group, or a derivative of any thereof.

In some embodiments, the selectively-reactive linker moiety of the modified trityl protecting group comprises a component of a click reaction.

In some embodiments, the modified trityl protecting group has the structure:

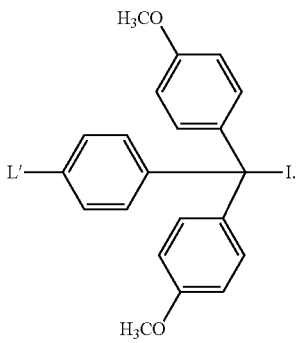

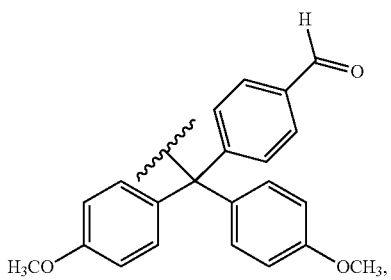

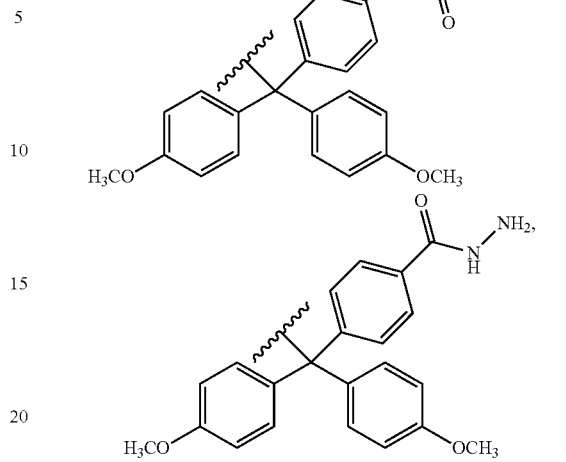

or a derivative thereof.

In some embodiments, the modified trityl protecting group does not comprise an N-hydroxy-succinimidyl group.

Methods of Synthesizing a Reactive Biopolymeric Compound

In another aspect are provided methods of synthesizing a reactive biopolymeric compound, for example methods for synthesizing any of the reactive biopolymeric compounds described above.

In these methods, the biopolymeric compound is a synthetic biopolymeric compound that has preferably been synthesized on a solid support, for example a solid synthetic support, using any suitable solid-phase synthetic method. In particular, a synthetic biopolymeric compound of any desired sequence can be prepared by the stepwise addition of reactive monomeric units to a functional residue, for example a nucleophilic residue, that is covalently attached to the solid support. Such approaches are well known and understood by those of ordinary skill in the art. Each reactive monomeric unit used in the synthetic method preferably comprises at least two functional groups, one that is reactive with the immobilized functional residue on the solid support and one that is modified with a protecting group. Where the immobilized functional residue is a nucleophilic residue, the reactive functional group of the reactive monomeric unit is preferably an electrophilic group.

After coupling the reactive monomeric unit to the immobilized functional residue, the solid support can be washed to remove excess reagents and any other soluble impurities, and any remaining unreacted functional residues on the solid support can be capped in order to prevent the subsequent extension of incorrect sequences. Selective deprotection, often known as deblocking by those of ordinary skill in the art, of the newly-added monomeric unit on the immobilized biopolymeric compound reveals a new functional residue and allows the next reactive monomeric unit to be added to the growing chain on the solid support. Other reactive functional groups on the immobilized biopolymeric compound, for example functional groups on side chains of the compound, can be modified with protecting groups that remain associated with the synthetic biopolymeric compound until the synthetic process is complete. Further chemical transformations, for example oxidation of the polymeric backbone, may be carried out in order to achieve a final desired product. These reactions may be performed either before or after cleavage of the biopolymeric compound from the synthetic support, as is understood by those of ordinary skill in the art. Some of the above reactions may include catalysts or other supplemental chemical agents to achieve optimal results.

Solid-phase synthetic approaches have been widely used for many years with great success to prepare synthetic polypeptides and oligonucleotides, including ribonucleotides and deoxyribonucleotides. These approaches can be extended and adapted for use with these, and other, biopolymeric compounds in the synthetic methods described herein. Specifically, in the instant methods, a synthetic support is typically provided that comprises a biopolymeric compound, preferably a synthetic biopolymeric compound. The biopolymeric compound comprises a first terminus that is attached to the solid support and a reactive second terminus, which may be the same functional group that was used to attach reactive monomeric units to the biopolymer during a solid-phase synthetic process. The second terminus is reacted under suitable conditions with a reagent compound that comprises a modified trityl protecting group that further comprises a selectively-reactive linker moiety, for example any of the modified trityl protecting groups described above. Covalent attachment of the reagent compound to the immobilized biopolymeric compound generates an immobilized reactive biopolymeric compound, as would be understood by those of ordinary skill in the art.

The reagent compound comprising a modified trityl protecting group that is used to prepare the immobilized reactive biopolymeric compounds in these methods can utilize the same chemical reactivity that was used to generate the synthetic biopolymeric compound itself. For example, where the synthetic biopolymeric compound is a synthetic oligonucleotide or morpholino oligonucleotide, the reagent compound can be any of the phosphoramidite or phosphoramidate reagent compounds described above. As was described in detail previously, these reagent compounds can react with a free functional group of an immobilized oligonucleotide to generate an immobilized reactive oligonucleotide or morpholino oligonucleotide.

It should also be understood, however, that the modified trityl protecting group can be attached to an immobilized biopolymeric compound using any suitable chemistry. For example, where the immobilized biopolymeric compound comprises any type of reactive functionality on its free terminus, a reagent compound comprising the modified trityl protecting group and a suitable reactive moiety can be designed to modify that specific reactive functionality.

In preferred methods, after attachment of the modified trityl protecting group to the immobilized biopolymeric compound, the compound is cleaved from the synthetic support under conditions where the modified trityl protecting group remains attached to the synthetic biopolymeric compound. The cleaved reactive synthetic biopolymeric compound is thus available for purification using the capture and release methods described in detail herein.

In some embodiments, the immobilized reactive biopolymeric compound is an immobilized reactive oligonucleotide, and the methods of synthesis can be as shown in FIGS. 1A and 1B. In these methods, the final "on synthesizer" step of the synthesis involves the reaction of a phosphoramidite reagent compound, for example any of the above-described phosphoramidite reagent compounds, with the 5' end of a synthetic oligonucleotide that remains immobilized via its 3' end on a synthetic support. The 5'-hydroxyl of the phosphoramidite reagent compound comprises a modified trityl protecting group (i.e., either the "X" group of FIG. 1A or the modified trityl group of FIG. 1B).

The synthetic oligonucleotide on the solid support is accordingly reacted with any of the above-described phosphoramidite reagent compounds to extend the oligonucleotide from the 5'-terminus of the immobilized synthetic oligonucleotide. After the solid support has been washed to remove excess reagent compounds and any soluble side-products of the reaction, the extended oligonucleotide, which now comprises a selectively-reactive linker moiety and is thus a "reactive" oligonucleotide, can be cleaved from the solid support. In some embodiments, the oligonucleotide is cleaved from the solid support using standard cleavage methods. In other embodiments, the cleaving step is performed simultaneously as the nucleobase deprotection step. In still other embodiments, the cleavage and nucleobase deprotection are accomplished using mild cleavage and deprotection conditions, including 0.05 M potassium carbonate in methanol, methylamine, or methylamine/ammonium hydroxide, in order to minimize any possible degradation reactions.

The methods of synthesis generally follow the synthesis and cleavage steps illustrated in FIGS. 1A and 1B. The reactive oligonucleotides produced by these methods can optionally be deprotected prior to their purification by the instant capture and release methodology. In some embodiments, the reactive oligonucleotides can alternatively remain in the nucleobase-protected form until after the capture and release purification of these oligonucleotides is complete.

The modified trityl protecting groups used in these methods, and the selectively-reactive linker moieties included within these protecting groups, can be any of the above-described groups and moieties, without limitation, as would be understood by those of ordinary skill in the art.

It should also be understood that although the methods of synthesizing reactive biopolymeric compounds have been illustrated using the examples of reactive oligonucleotide compounds, these methods are widely adaptable to the synthesis of any reactive biopolymer, including, for example, reactive polypeptides, reactive oligosaccharides, reactive morpholino oligonucleotides, and any other reactive biopolymer that can be prepared using the above-described solid-phase synthetic methodologies.

Methods of Purifying a Reactive Biopolymeric Compound

In another aspect are provided methods of purifying a reactive biopolymeric compound. These methods generally comprise the step of providing a reactive biopolymeric compound, for example any of the reactive biopolymeric compounds described above, and reacting the reactive biopolymeric compound with a solid support comprising a reactive oxyamino group, a reactive hydrazino group, a reactive carbonyl group, or a component of a click reaction. As has been described in detail above, the selectively-reactive linker moieties of the reactive biopolymeric compounds are chosen to be complementary to the reactive groups associated with the capture support. For example, if the selectively-reactive linker moiety of the reactive biopolymeric compound comprises a reactive carbonyl group, such as a suitable formyl group, the capture support preferably comprises a reactive oxyamino group or a reactive hydrazino group, as would be understood by those of ordinary skill in the art in view of the instant disclosure. Alternatively, if the selectively-reactive linker moiety of the reactive biopolymeric compound comprises a reactive oxyamino group or a reactive hydrazino group, the capture support preferably comprises a reactive carbonyl group, such as a suitable formyl group. Furthermore, if the selectively-reactive linker moiety of the reactive biopolymeric compound comprises a reactive azide, the capture support could comprise a reactive alkyne or strained alkyne group. Alternatively, if the selectively-reactive linker moiety of the reactive biopolymeric compound comprises a reactive alkyne or strained alkyne group, the capture support could comprise a reactive azide group.

After the reactive biopolymeric compound has been captured by reaction with the suitably-reactive capture support, the capture support can be washed, for example to remove failure sequences or other impurities. While the reactive biopolymeric compound remains linked to the suitably-reactive capture support, it may additionally be modified by treatment with chemical compounds or enzymes to add or remove a chemical modification. For example, the tethered biopolymeric compound can be equilibrated with an appropriate reaction buffer, treated with a chemically reactive fluorophore or quencher, a chemically reactive biotin, a chemically reactive biopolymer such as a hapten, or a chemically reactive linker, or subjected to a kinase, capping enzyme, or other enzyme along with substrates and cofactors as required to modify the biopolymer. Following treatment with such compounds or enzymes, excess reagents can be washed away prior to cleavage of the modified biopolymeric compound from the capture support.

After the captured and optionally modified biopolymeric compound has been washed, it can be released from the capture support, either by a soft release, which reverses the capture reaction without cleaving the modified trityl group from the terminus of the biopolymeric compound, or by a hard release, which generates a purified, fully-deprotected biopolymeric compound. In some embodiments, a soft release of the biopolymeric compound that retains the trityl protecting group can be performed either by cleaving a linker that joins the trityl group to the selectively-reactive linker moiety, by cleaving a linker that joins the complementary selectively-reactive linker moiety to the capture support, or by dispersing or solubilizing the capture support. For example, the linker joining the trityl group to the selectively-reactive linker moiety or the complementary selectively-reactive linker moiety to the capture support can be an enzymatically cleavable linker, a photocleavable linker, a disulfide bridge, an azo compound, a phenacyl ester, an ortho-nitrobenzyl derivative, or any other suitable cleavable linker known to those of average skill in the art. See, e.g., Leriche et al. (2012) *Bioorg. Med. Chem.* 20 571-582 and Bargh et al. (2019) *Chem. Soc. Rev.,* 48, 4361. Accordingly, in some embodiments, the releasing step is performed using an agent that causes dissociation of any bond between the trityl group and the capture support. In some embodiments, the releasing step includes the deprotection of the biopolymeric compound using, for instance, a mild acid solution to break the bond between the protecting group and the terminus of the biopolymeric compound.

The methods of purification thus generally follow the capture and release techniques described above, and as illustrated, for example, in FIGS. 1A and 1B.

In more specific embodiments, the reactive biopolymeric compound is a reactive oligonucleotide, a reactive polypeptide, a reactive oligosaccharide, or a reactive morpholino oligonucleotide.

In some aspects, the disclosure provides novel compounds and methods according to the following numbered paragraphs:

1. A reagent compound having a structure:

T'-X wherein T' is a modified trityl protecting group comprising a selectively-reactive linker moiety and X is a leaving group.

2. The reagent compound of paragraph 1, wherein T' has a structure:

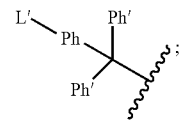

wherein L' comprises the selectively-reactive linker moiety, Ph is an optionally substituted phenylene moiety, and each Ph' is independently an optionally substituted phenyl group.

3. The reagent compound of paragraph 2, wherein each Ph' is independently substituted with one or more $C_1$-$C_4$ alkoxy groups, one or more $C_1$-$C_4$ alkyl groups, or a combination of $C_1$-$C_4$ alkoxy groups and $C_1$-$C_4$ alkyl groups.

4. The reagent compound of paragraph 3, wherein the modified trityl protecting group has a structure:

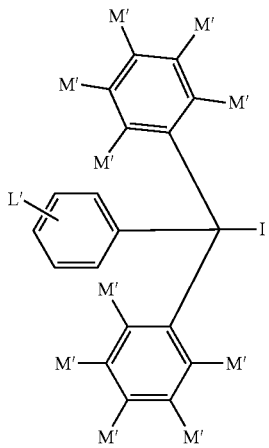

wherein each M' is independently a $C_1$-$C_4$ alkoxy group, a $C_1$-$C_4$ alkyl group, —H, or a combination thereof.

5. The reagent compound of paragraph 4, wherein at least one M' is a methoxy group.

6. The reagent compound of paragraph 5, wherein the modified trityl protecting group has a structure:

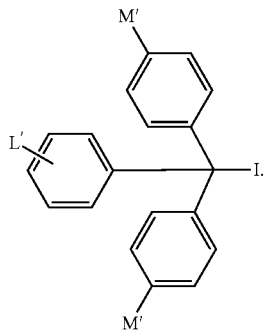

7. The reagent compound of paragraph 6, wherein the modified trityl protecting group has a structure:

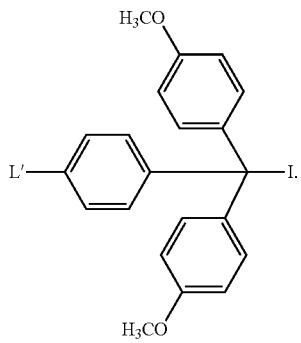

8. The reagent compound of paragraph 1, wherein X is a halo group.
9. The reagent compound of paragraph 8, wherein the halo group is a fluoro or a chloro group.
10. The reagent compound of paragraph 1, wherein X is an acyl leaving group.
11. The reagent compound of paragraph 10, wherein the acyl leaving group is an acetyl or trihaloacetyl leaving group.
12. The reagent compound of paragraph 1, wherein the modified trityl protecting group does not comprise an N-hydroxy-succinimidyl group.
13. The reagent compound of any one of paragraphs 1-12, wherein the selectively-reactive linker moiety comprises a reactive carbonyl group, a reactive oxyamino group, a reactive hydrazino group, a component of a click reaction, or a derivative of any thereof.
14. The reagent compound of paragraph 13, wherein the selectively-reactive linker moiety comprises:

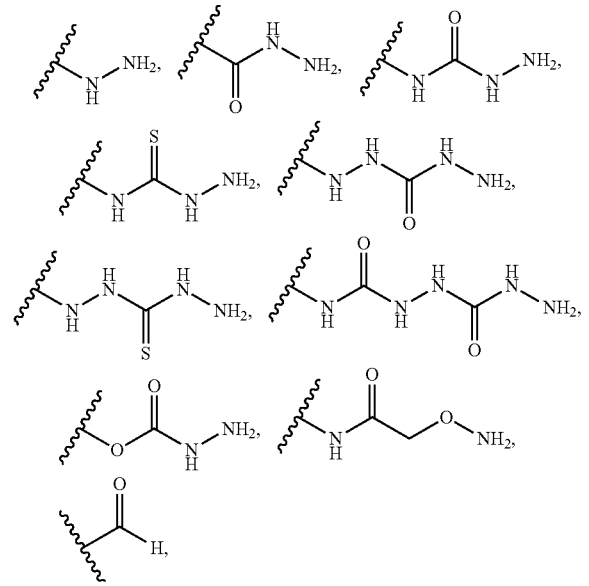

or a derivative of any thereof.
15. A reactive biopolymeric compound having a structure:

T'-BP';

wherein T' is a modified trityl protecting group comprising a selectively-reactive linker moiety and BP' is a biopolymer.

16. The reactive biopolymeric compound of paragraph 15, wherein T' has a structure:

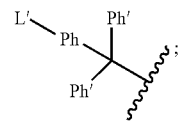

wherein L' comprises the selectively-reactive linker moiety, Ph is an optionally substituted phenylene moiety, and each Ph' is independently an optionally substituted phenyl group.
17. The reactive biopolymeric compound of paragraph 16, wherein each Ph' is independently substituted with one or more $C_1$-$C_4$ alkoxy groups, one or more $C_1$-$C_4$ alkyl groups, or a combination of $C_1$-$C_4$ alkoxy groups and $C_1$-$C_4$ alkyl groups.
18. The reactive biopolymeric compound of paragraph 17, wherein the modified trityl protecting group has a structure:

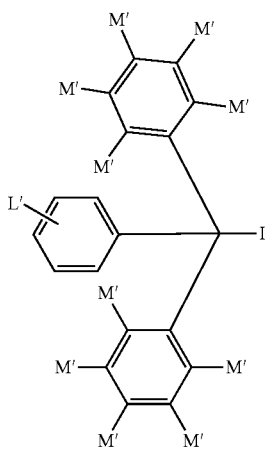

wherein each M' is independently a $C_1$-$C_4$ alkoxy group, a $C_1$-$C_4$ alkyl group, —H, or a combination thereof.
19. The reactive biopolymeric compound of paragraph 18, wherein at least one M' is a methoxy group.
20. The reactive biopolymeric compound of paragraph 19, wherein the modified trityl protecting group has a structure:

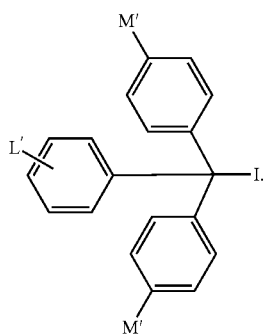

21. The reactive biopolymeric compound of paragraph 20, wherein the modified trityl protecting group has a structure:

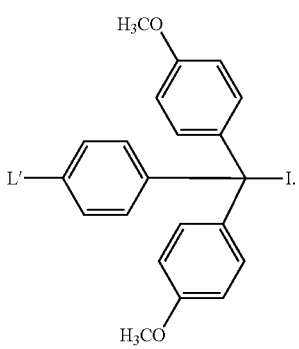

22. The reactive biopolymeric compound of paragraph 15, wherein the biopolymer is an oligonucleotide, a polypeptide, an oligosaccharide, or a morpholino oligonucleotide.

23. The reactive biopolymeric compound of paragraph 22, wherein the biopolymer is an oligonucleotide.

24. The reactive biopolymeric compound of paragraph 15, wherein the modified trityl protecting group does not comprise an N-hydroxy-succinimidyl group.

25. The reactive biopolymeric compound of paragraph 15, wherein the compound comprises a terminus attached to a solid support.

26. The reactive biopolymeric compound of any one of paragraphs 15-25, wherein the selectively-reactive linker moiety comprises a reactive carbonyl group, a reactive oxyamino group, a reactive hydrazino group, a component of a click reaction, or a derivative of any thereof.

27. The reactive biopolymeric compound of paragraph 26, wherein the selectively-reactive linker moiety comprises:

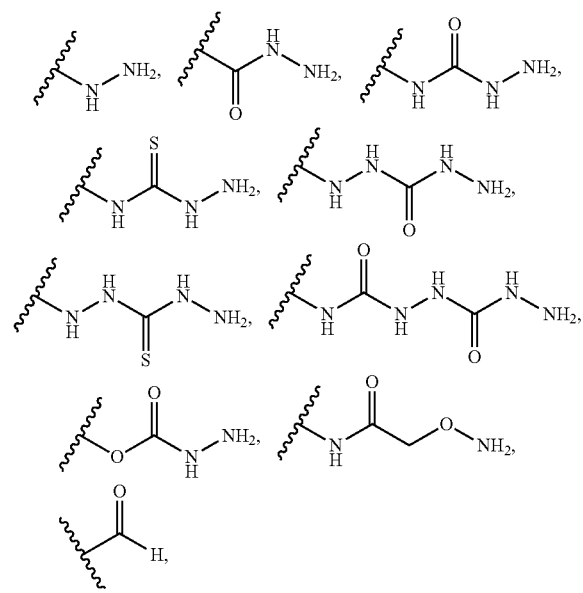

or a derivative of any thereof.

28. A method of synthesizing a reactive biopolymeric compound comprising the steps of:
   a) providing a solid support comprising a biopolymer, wherein the biopolymer is attached to the solid support at a first terminus; and
   b) reacting a second terminus of the biopolymer with a reactive reagent comprising a modified trityl protecting group comprising a selectively-reactive linker moiety to generate an immobilized reactive biopolymeric compound.

29. The method of paragraph 28, further comprising the step of cleaving the immobilized reactive biopolymeric compound from the solid support.

30. The method of paragraph 29, further comprising the step of deprotecting the reactive biopolymeric compound without removing the modified trityl protecting group.

31. The method of paragraph 30, wherein the cleaving step and the deprotecting step are performed simultaneously.

32. The method of paragraph 28, wherein the biopolymer is a synthetic biopolymer.

33. The method of paragraph 28, wherein modified trityl protecting group has a structure:

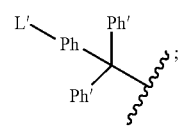

wherein L' comprises the selectively-reactive linker moiety, Ph is an optionally substituted phenylene moiety, and each Ph' is independently an optionally substituted phenyl group.

34. The method of paragraph 33, wherein each Ph' is independently substituted with one or more $C_1$-$C_4$ alkoxy groups, one or more $C_1$-$C_4$ alkyl groups, or a combination of $C_1$-$C_4$ alkoxy groups and $C_1$-$C_4$ alkyl groups.

35. The method of paragraph 34, wherein the modified trityl protecting group has a structure:

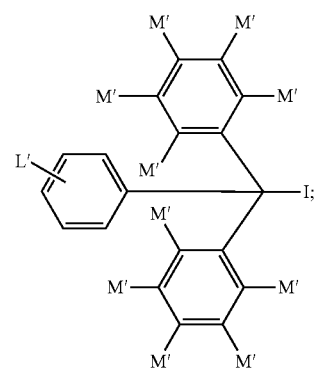

wherein each M' is independently a $C_1$-$C_4$ alkoxy group, a $C_1$-$C_4$ alkyl group, —H, or a combination thereof.

36. The method of paragraph 35, wherein at least one M' is a methoxy group.

37. The method of paragraph 36, wherein the modified trityl protecting group has a structure:

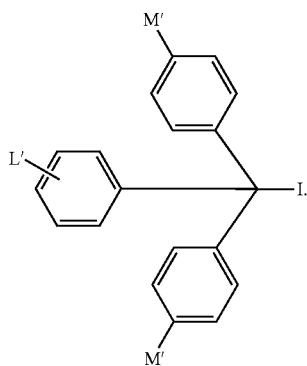

38. The method of paragraph 37, wherein the modified trityl protecting group has a structure:

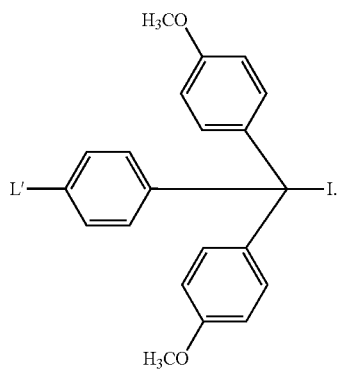

39. The method of paragraph 28, wherein the biopolymer is an oligonucleotide, a polypeptide, an oligosaccharide, or a morpholino oligonucleotide.

40. The method of paragraph 39, wherein the biopolymer is an oligonucleotide.

41. The method of paragraph 28, wherein the modified trityl protecting group does not comprise an N-hydroxy-succinimidyl group.

42. The method of any one of paragraphs 28-41, wherein the selectively-reactive linker moiety comprises a reactive carbonyl group, a reactive oxyamino group, a reactive hydrazino group, a component of a click reaction, or a derivative of any thereof.

43. The method of paragraph 42, wherein the selectively-reactive linker moiety comprises:

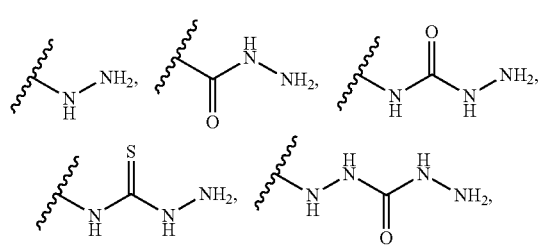

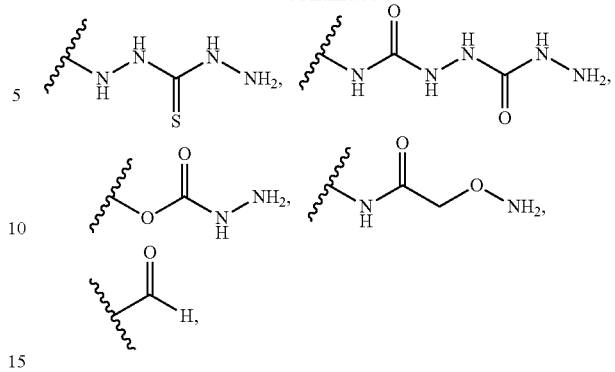

or a derivative of any thereof.

44. A method of purifying a biopolymeric compound comprising the steps of:
   a) providing a reactive biopolymeric compound of any one of paragraphs 15-27; and
   b) reacting the reactive biopolymeric compound with a solid support comprising a reactive oxyamino group, a reactive hydrazino group, a reactive carbonyl group, or a component of a click reaction to selectively bind the reactive biopolymeric compound to the solid support.

45. The method of paragraph 44, further comprising the step of washing the solid support.

46. The method of paragraph 45, further comprising the step of releasing the selectively-bound biopolymeric compound from the solid support.

47. The method of paragraph 45, further comprising the step of deprotecting the selectively-bound biopolymeric compound.

48. The method of paragraph 47, wherein the cleaving step and the deprotecting step are performed simultaneously.

49. The method of paragraph 44, wherein the selectively-reactive linker moiety comprises a reactive carbonyl group, a reactive oxyamino group, a reactive hydrazino group, a component of a click reaction, or a derivative of any thereof.

50. The method of paragraph 49, wherein the selectively-reactive linker moiety comprises:

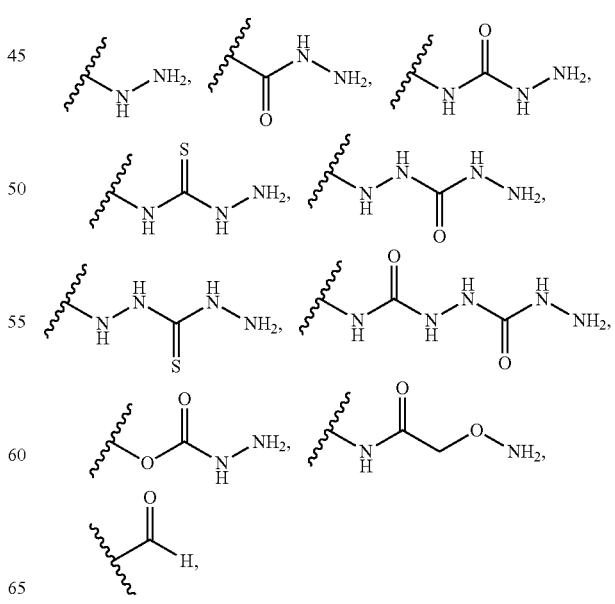

or a derivative of any thereof.

It will be readily apparent to one of ordinary skill in the relevant arts that other suitable modifications and adaptations to the compounds, methods, and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Synthesis of a 4-Formyl-DMT Protecting Group and its Incorporation on a Nucleoside Synthesis of a 4-formyl-DMT dT phosphoramidite was performed, as described below, at room temperature except as specified, and as illustrated in Scheme 1.

1-2: 1-dimethoxyacetal-4-bromobenzene: To a solution of 1-formyl-4-bromobenzene (31.5 g; 0.175 mol) in methanol (100 mL) was added dropwise trimethylorthoformate (32.0 mL; 0.19 mol) followed by 4 N HCl/dioxane (1.0 mL). The reaction was stirred at room temperature for 2 h. TLC (hexane/ethyl acetate (9/1)) indicated complete conversion to product. The solvent was removed on the rotavap to yield a pale yellow oil. The product was dissolved in dichloromethane (100 mL) and washed with saturated sodium bicarbonate and brine (75 mL each), dried over anhydrous magnesium sulfate, filtered and concentrated to yield the desired product (35 g). $^1$H NMR indicated no impurities and the product was used without purification.

1-3: To a flask dried under argon was added magnesium turnings dried overnight under high vacuum (750 mg; 32.5 mmol), anhydrous THF (40 mL), and 1,2-diiodoethane (few crystals). Added 1-dimethoxyacetal-4-bromobenzene (1-2; 8.3 g; 35.8 mmol). The flask was placed in a sonicator bath and heated to 60° C. with sonication. Following heating for 30 min significant bubbling initiated. Sonication was continued until bubbling ceased and all magnesium was consumed. To the reaction mixture was added a slurry of dried 4,4'-dimethoxybenzophenone (1-1) (7.5 g; 31.0 mmol) portion wise suspended in anhydrous THF (10 mL). The reaction mixture was stirred at room temperature for 90 min. TLC (hexane/ethyl acetate (2/1)) indicated near complete consumption of 4,4'-dimethoxybenzophenone. To the reaction mixture was added 0.6 N HCl (50 mL) and ethyl acetate (75 mL). The reaction mixture was transferred to a separatory funnel. The phases were separated and the organic phase was washed with saturated sodium bicarbonate (50 mL) and brine (50 mL). The organic phase was dried over anhydrous sodium sulfate, filtered and concentrated to yield 12.5 g of a thick yellow oil. 1-3 (6.2 g) was isolated by silica chromatography using hexane/ethyl acetate (3/1) as eluant. NMR indicated the product was a 3/1 acetal/aldehyde mixture.

The product mixture (3.30 g; 8.3 mmol) was dissolved in acetone (12 mL) and 4 N HCl (20 µL) was added. On addition the reaction mixture turned reddish but following stirring became clear. TLC (hexane/ethyl acetate (2/1)) indicated complete conversion to aldehyde. The reaction mixture was concentrated to yield 1-4 as a reddish oil.

1-6: 1-4 (2.90 g; 83.2 mmol) was dissolved in anhydrous dichloromethane (15 mL). With stirring added trifluoroacetic acid (1.8 mL) dropwise by syringe. Stirring was continued for 1 h. The reaction mixture was concentrated on the rotavap to yield a very thick dark red oil. The oil was dissolved in anhydrous THF (10 mL) and placed under argon. The flask was vortexed to dissolve the oil. To a separate flask was added thymidine (1-5) (2.02 g; 83.2 mmol) and a stirring bar and placed on the rotavap under reduced pressure for 1 h to dry. To the thymidine flask was added anhydrous THF (15 mL), diisopropylethylamine (2.9 mL; 0.017 mmol) followed by dropwise addition of the activated alcohol. The color was immediately quenched and stirring was continued for 45 min. TLC (dichloromethane/MeOH/TEA (90/10/1)) indicated excellent conversion to product. The reaction mixture was concentrated to half volume on the rotavap and partitioned between dichloromethane (100 mL) and 0.6 N HCl (50 mL). Following separation, the organic phase was washed with saturated sodium bicarbonate solution and brine (50 mL each). The organic phase was dried over anhydrous sodium sulfate, filtered and concentrated to yield 3.4 g of a thick yellow oil. Desired product was isolated by silica gel chromatography. Initially the silica gel was washed with hexane/TEA (90/10) followed by washing with hexane/ethyl acetate. The crude product was added to the column and eluted with hexane/ethyl acetate (90/10). Fractions containing the product were combined and concentrated to yield 1.2 g of a white solid.

1-8: To a solution of 4FB-DMT-thymidine (1.2 g) dried at 40° C. for 30 min on the rotavap was added anhydrous dichloromethane (25 mL) and diisopropylethylamine (0.44 mL) and phosphonamidic chloride ($^1$H 1-7; 0.54 mL). The reaction mixture was stirred at room temperature for 2.5 h. TLC (hexane/ethyl acetate (1/2); triethylamine quenched TLC plate). The reaction mixture was diluted with dichloromethane (20 mL) and washed with saturated sodium bicarbonate (20 mL) and brine (20 mL). The organic phase was dried over anhydrous sodium sulfate, filtered and concentrated to yield 1.7 g of a pale yellow oil. The product was isolated by silica gel chromatography. The silica gel was pre-treated with 5% triethylamine in hexane and washed with hexanes followed by hexane/ethyl acetate (1/1). The crude product was added to the column and eluted with hexane/ethyl acetate (1/2). Fractions containing the product were combined and concentrated on the rotavap to yield 1.2 g of desired product as confirmed by $^1$H and $^{31}$P NMR.

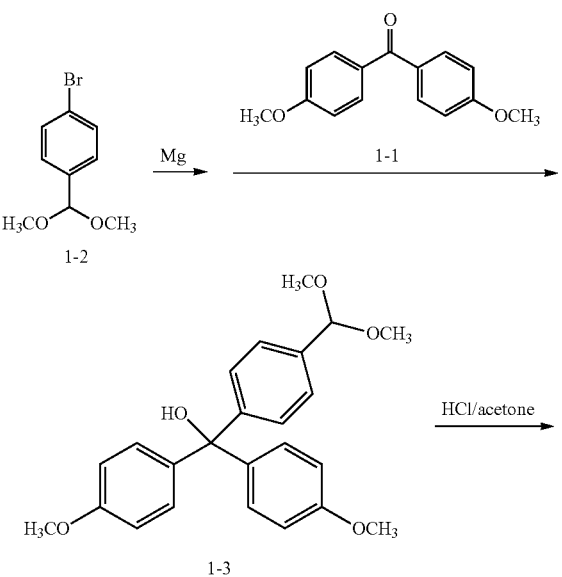

Scheme 1

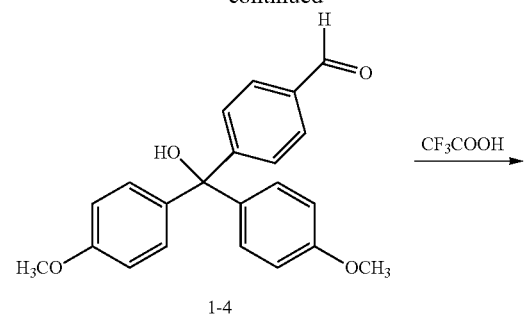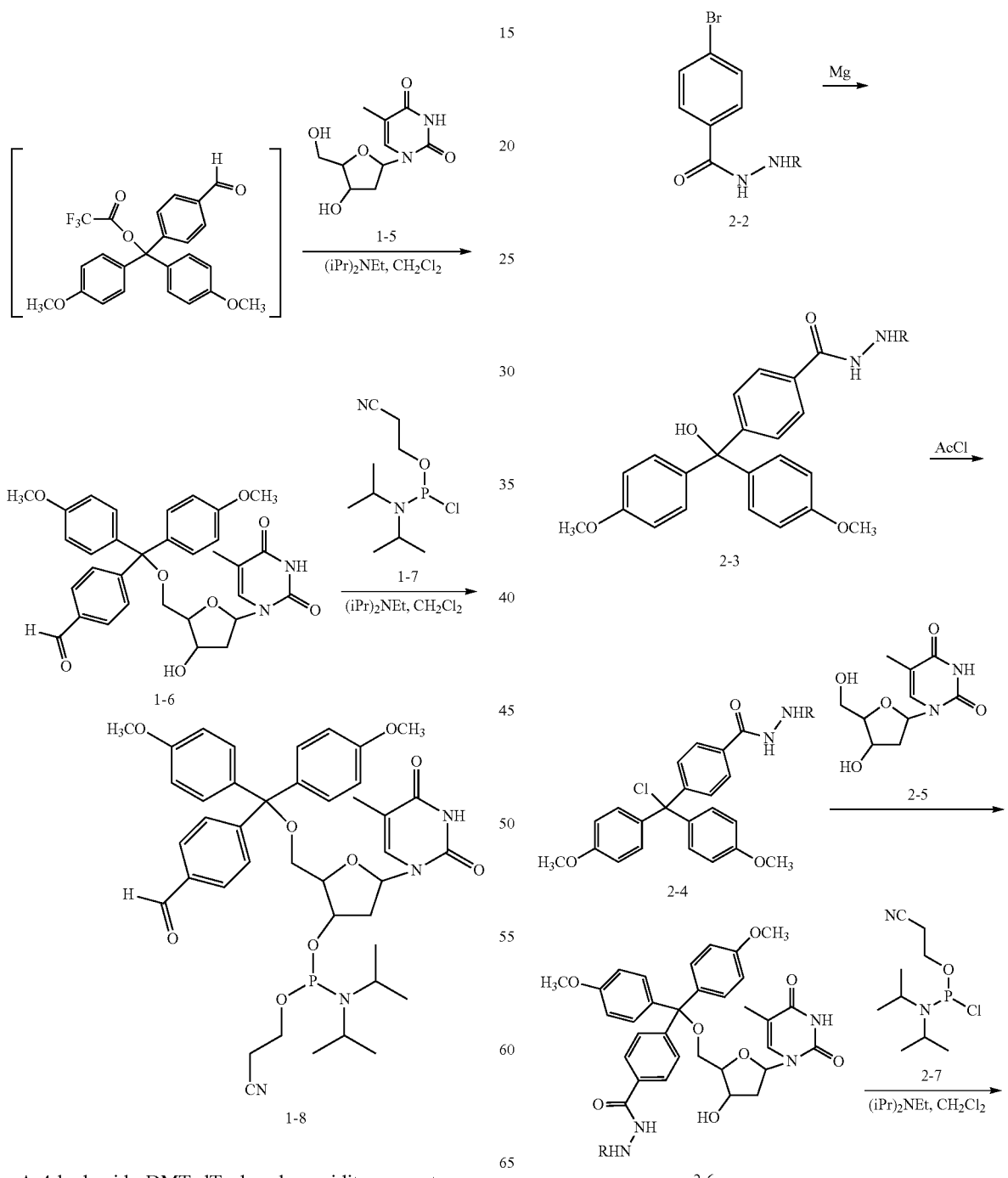
A 4-hydrazido-DMT dT phosphoramidite reagent compound is prepared as illustrated in Scheme 2.

-continued

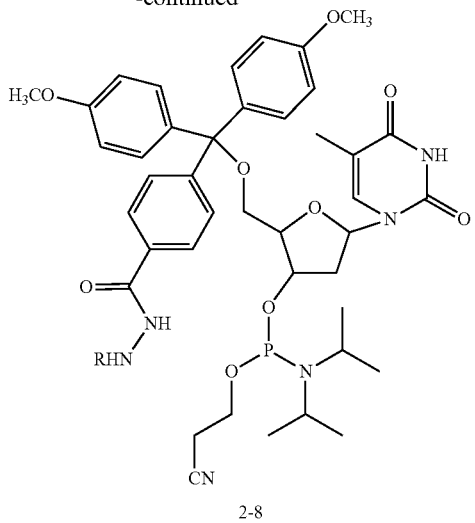

2-8

4-formyl-DMT-ON Oligonucleotide dT (25-mer) Synthesis

To demonstrate efficient "capture-and-release" purification of nucleic acids using the described technology, a 25-mer dT oligonucleotide was synthesized by reacting a 4-formyl-DMT dT phosphoramidite with the 5'-terminus of a 24-mer dT oligonucleotide in the last synthetic step:

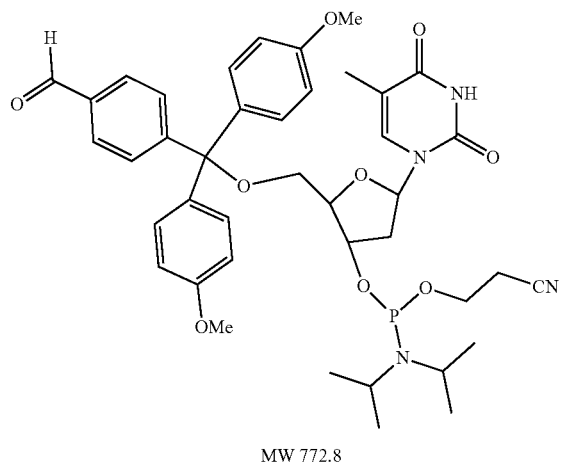 [SMILES: COc1ccc(C(OCC2OC(n3cc(C)c(=O)[nH]c3=O)CC2OP(OCCC#N)N(C(C)C)C(C)C)(c2ccc(C=O)cc2)c2ccc(OC)cc2)cc1]

MW 772.8

4-formyl-DMT dT phosphormdite

The oligonucleotide was produced on a MerMade™ 12 synthesizer according to the manufacturer's recommendations using a 1 µmol, 1,000-Angstrom controlled pore glass (CPG) dT solid support column (Glen Research; Sterling, VA; catalog number 20-2031). After removing the 5' dimethoxytrityl protecting group from the CPG-bound dT residue, twenty-three monomer addition cycles were performed using dT-phosphoramidite (Glen Research; catalog number 10-1030), followed by a single addition of 4-formyl-DMT dT phosphoramidite. The capping steps using acetic anhydride in acetonitrile (ACN) were omitted for the last two base additions. β-cyanoethyl protecting groups were removed from the backbone phosphates using 10% diethylamine (DEA) in ACN for 5 minutes at room temperature, followed by an ACN flush to remove excess DEA, prior to cleavage of the oligonucleotide and any failure sequences (crude oligonucleotide) from the CPG support. The crude oligonucleotide was cleaved "DMT-ON" via incubation of the CPG in approximately 0.75 mL of concentrated ammonia at room temperature for 1 hour. After cleavage, the ammonia solution was transferred to a new tube, and Tris base was added to a concentration of 40 mg/mL to prevent possible 4-formyl-DMT loss during dry-down of the oligonucleotide due to acidification. This solution was reduced to dryness under a stream of nitrogen at room temperature.

4-formyl-DMT-ON Oligonucleotide dT (25-mer) Desalting

Prior to mass spectrometry (MS) analysis and purification of the full-length oligonucleotide, Tris base was removed and the crude oligonucleotide exchanged into a suitable buffer via diafiltration. 2 mM triethylamine (TEA) was prepared by adding 13.94 µL neat TEA to 50 mL nuclease-free water with mixing. Dried crude oligonucleotide sample was dissolved in 450 µL of 2 mM TEA and read on a spectrophotometer at 1/100 dilution. The sample had a 1-cm absorbance value of 2.278, which is equal to 102.5 $OD_{260}$ units (3.81 mg; 26.93 OD/mg) of crude oligonucleotide. The sample was desalted three times (10-fold reduction in volume each) into 2 mM TEA using a 0.5 mL, 5 kDa diafiltration apparatus. A small amount of white precipitate was observed in the retentate, which was removed by transferring to an Eppendorf tube and centrifuging at 16,000×g for 10 minutes. The clear supernatant was transferred to a new 0.5 mL, 5 kDa diafiltration apparatus and desalted a further two times into 2 mM TEA.

Figure 2A:
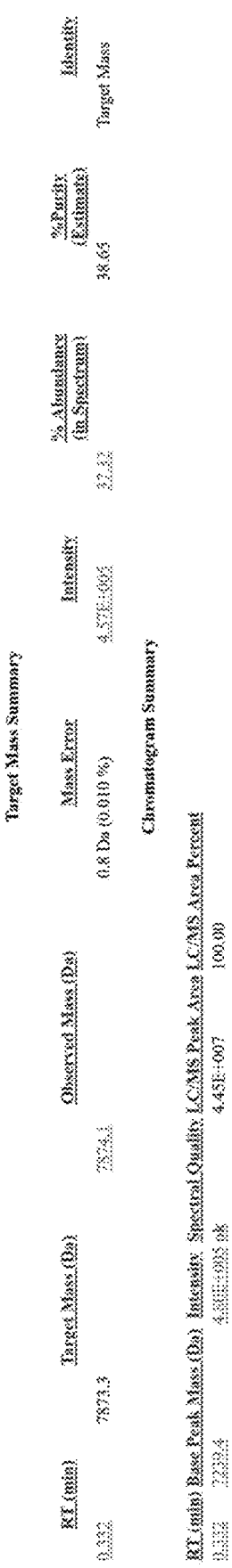
FIG. 2A. Mass spectrometric purity analysis of a desalted crude 4FB-DMT-ON dT 25-mer oligonucleotide.
Figure 2B:
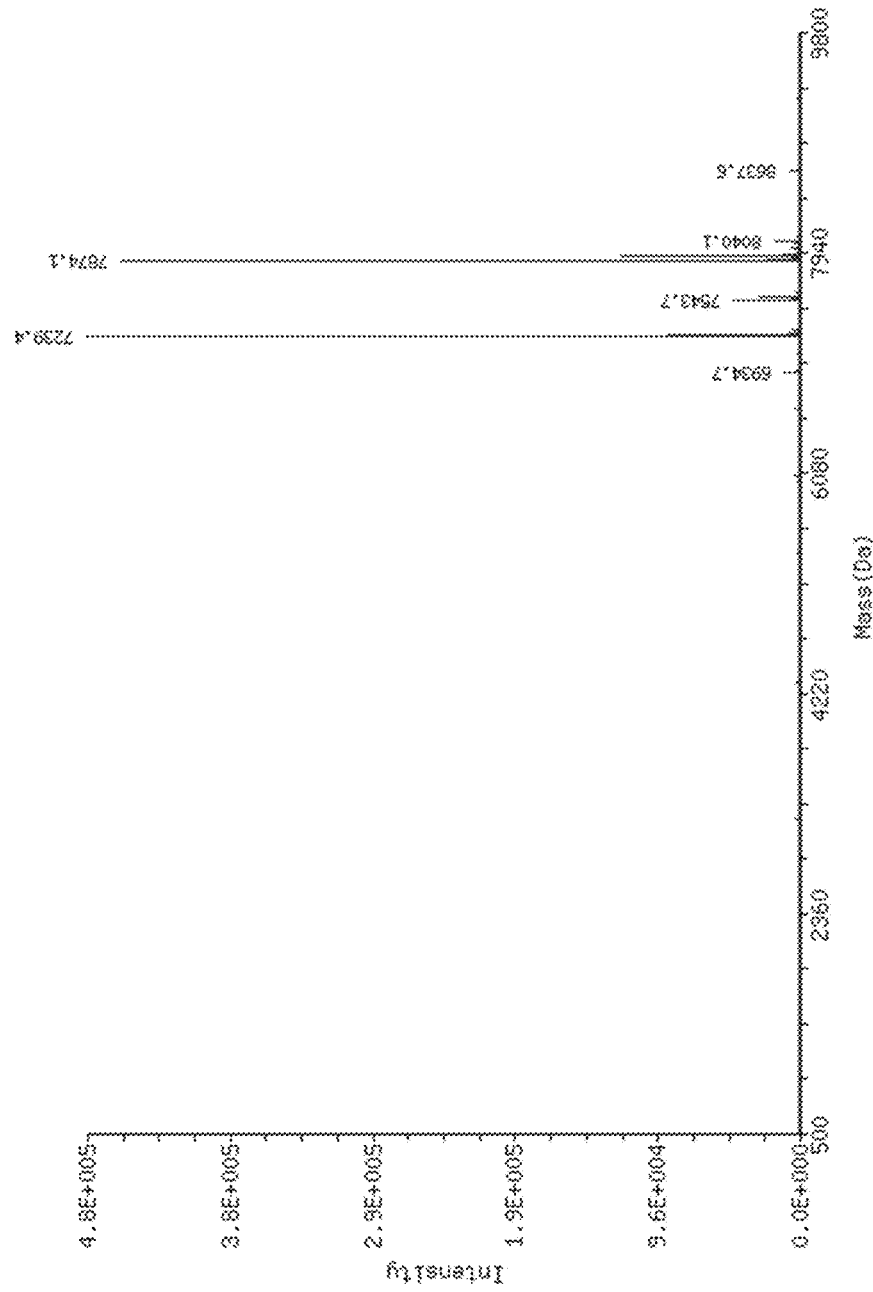
FIG. 2B. Deconvoluted mass spectrometric analysis of a desalted crude DMT-ON dT 25-mer oligonucleotide.
Figure 2C:
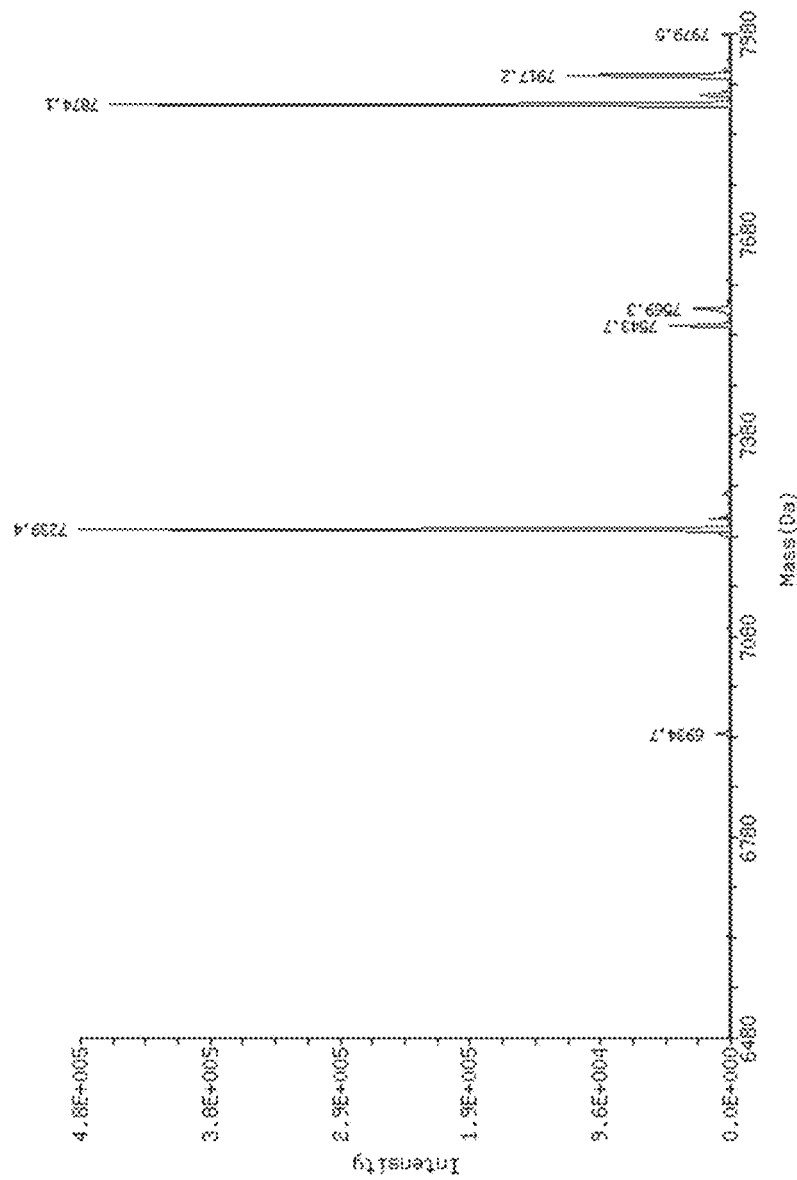
FIG. 2C. Zoomed deconvoluted mass spectrometric analysis of a desalted 4-formyl-DMT-ON dT 25-mer oligonucleotide.

Concentrated sample (approximately 50 µL) was transferred to a new Eppendorf tube and the diafiltration column was rinsed with 300 µL 2 mM TEA. Both were combined, and an aliquot was diluted 1/20 for $OD_{260}$ determination. Duplicate $A_{260}$ readings were 12.140 and 12.180, respectively, for an average of 0.243 OD/µL, which is equal to 85.1 $OD_{260}$ recovered for a desalt yield of 83.0%. A small portion of the desalted crude oligonucleotide sample was diluted to 500 ng/µL in 2 mM TEA for MS analysis (FIGS. 2A-2C). Purity was estimated to be 38.7% full-length DMT-ON product (target mass 7873.3 Da; observed mass 7874.1 Da). The major impurity was consistent with N-1 (dT 24-mer target mass 7238.7; observed mass 7239.4 Da). A minor impurity consistent with DMT-OFF full-length product (target mass 7542.9 Da; observed mass 7543.7) was also observed. A sample of this desalted crude solution was set aside for later ion-pairing ultra-performance liquid chromatography (IP-UPLC) analysis. Yield after removal of all analytical samples was 80.3 $OD_{260}$.

Capture and Release of the 4-formyl-DMT-ON Oligonucleotide dT (25-Mer)

Hydrazide resin was obtained from Thermo Scientific (catalog #: 53149). 500 µL of settled resin (1 mL of slurry) was removed to a 15 mL Falcon tube and washed twice by centrifugation at 3,000×g for 5 minutes each with 10 mL of Conjugation Buffer (CB; 100 mM sodium phosphate, 150 mM sodium chloride, pH 6.0). Washed resin was quantitatively transferred to a 2 mL cryovial. 80.3 $OD_{260}$ (330 µL; 2.98 mg) of the above crude oligonucleotide solution was mixed with an equal volume of CB. Diluted crude oligonucleotide solution was added to the hydrazide resin, and CB was added to create an approximately 35% resin suspension for the binding reaction. 70.5 µL Link Buffer (100 mM Aniline in CB) was added to catalyze hydrazone formation between the 4FB-DMT oligo and hydrazide resin. The reaction was mixed end-over-end at room temperature overnight at approximately 30 revolutions per minute.

The next day, the reaction was transferred to an Eppendorf tube and spun at 3,000×g to pellet resin. Clear supernatant was removed to an Eppendorf tube (850 µL). Approximately 1.25 mL of Modification Buffer (MB; 100 mM sodium phosphate, 150 mM sodium chloride, pH 8.0) was added to the resin. The slurry was mixed end-over-end at approximately 30 revolutions per minute on a rotator for 10 minutes, then briefly centrifuged at 3,000×g. Clear supernatant was removed to an Eppendorf tube (1.23 mL). Washing with 1.25 mL MB was repeated four additional times with 5-minute end-over-end mixing, centrifugation, and reserving the supernatant. The first supernatant and five wash supernatants were pooled into a 15 mL conical tube. This pool of unbound material of the crude oligonucleotide had a volume of approximately 9.0 mL and a 1-cm $A_{260}$ of 5.267. This is equivalent to approximately 47.4 $OD_{260}$, or approximately 59% of input crude oligonucleotide.

The resin was equilibrated with 1.5 mL of nuclease-free water twice with a 5-minute mix time between washes. Resin was subsequently equilibrated twice with 1.5 mL MES buffered saline (MBS; 100 mM MES, 150 mM sodium chloride, pH 4.7) with mixing, then briefly centrifuged at 3,000×g. A fresh 1.5 mL portion of MBS was added to the resin and the elution reaction was allowed to proceed for 48 hours at room temperature with slow end-over-end mixing. After centrifugation at 3,000×g, supernatant was removed to an Eppendorf tube, and 1.5 mL of fresh MBS was added to the resin. After end-over-end mixing for approximately 5 minutes, resin was centrifuged at 3,000×g and the supernatant was removed to a new Eppendorf tube. Resin was washed two additional times with 1.5 mL nuclease-free water to recover residual oligonucleotide. All MBS elution and water wash fractions were pooled in a 15 mL conical tube and had a total volume of 11.1 mL. The elution pool was basified by adding 1.0 mL of 1 M Tris base (final pH was approximately 9.0 by pH paper). The pool $A_{260}$ was read on a spectrophotometer to determine elution fraction yield, which was 24.7 $OD_{260}$ or approximately 31% of input crude oligonucleotide. If the elution fraction is considered to consist of full length oligonucleotide, this is equivalent to a 79% yield when factoring in the initial full-length DMT-ON product purity of 38.7% in the crude oligonucleotide. Resin was subsequently eluted with two 1.5 mL portions of 50% acetic acid, however no $A_{260}$ was detected in either of these fractions by spectrophotometry.

The unbound fraction and washes in Modification Buffer, as well as the neutralized elution pool above, were separately concentrated to approximately 400 µL using 6 mL, 3 kDa diafiltration apparatus. 2 mM TEA in nuclease-free water was added to each diafiltration apparatus Q.S. 6 mL, mixed well, and centrifuged until the retentate volume was <400 µL. This desalting process was repeated an additional three times with 2 mM TEA to remove all non-volatile salts in preparation for MS analysis. After desalting, the unbound fraction and eluted fraction samples were assayed on a spectrophotometer. Yield for the unbound fraction was 40.61 $OD_{260}$ (50.6% of input), and yield of the eluted fraction was 24.16 $OD_{260}$ (30.1% of input), for an overall yield of 80.7% between the two.

Figure 3B:
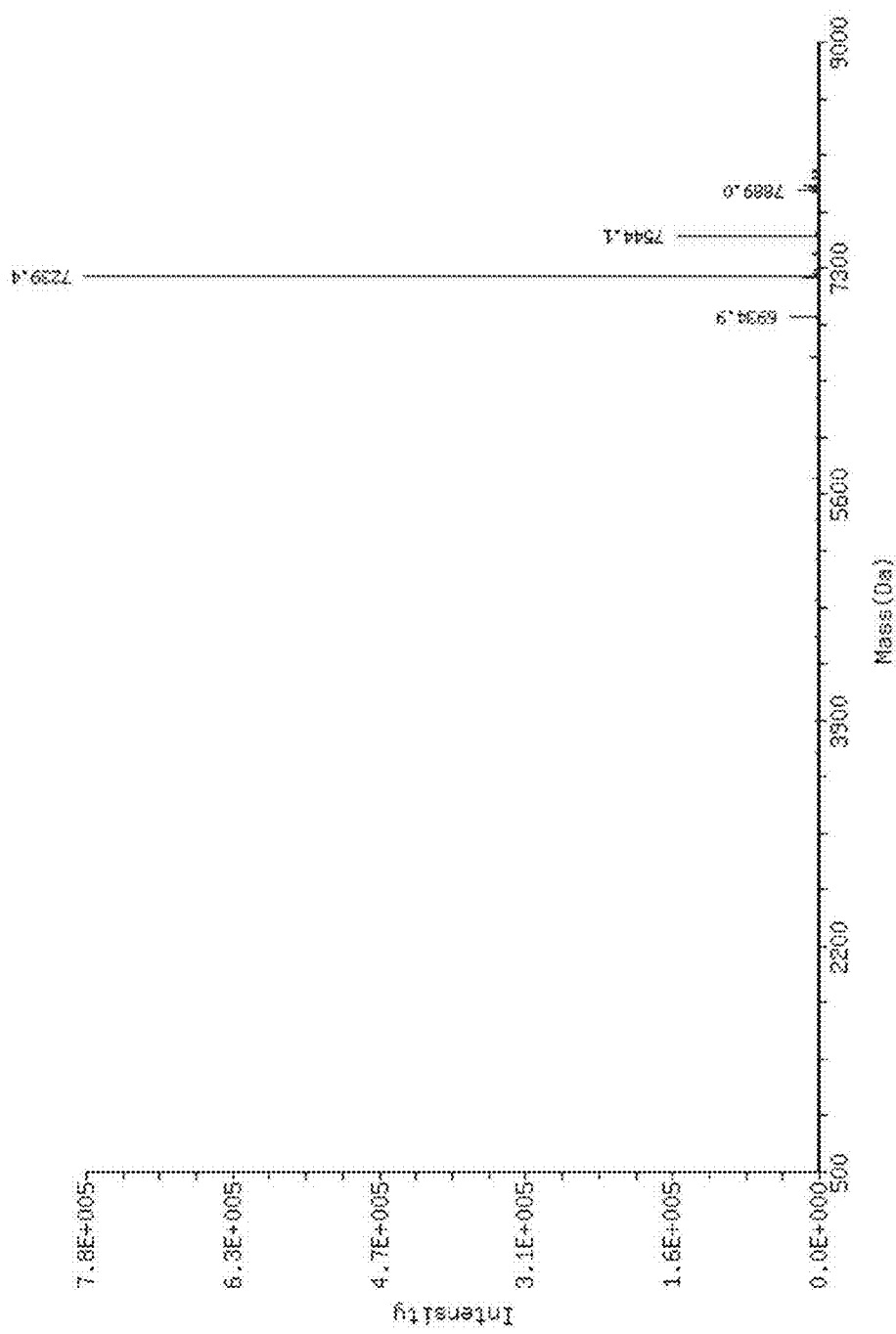
FIG. 3B. Deconvoluted mass spectrometric analysis of a desalted unbound oligonucleotide.
Figure 3C:
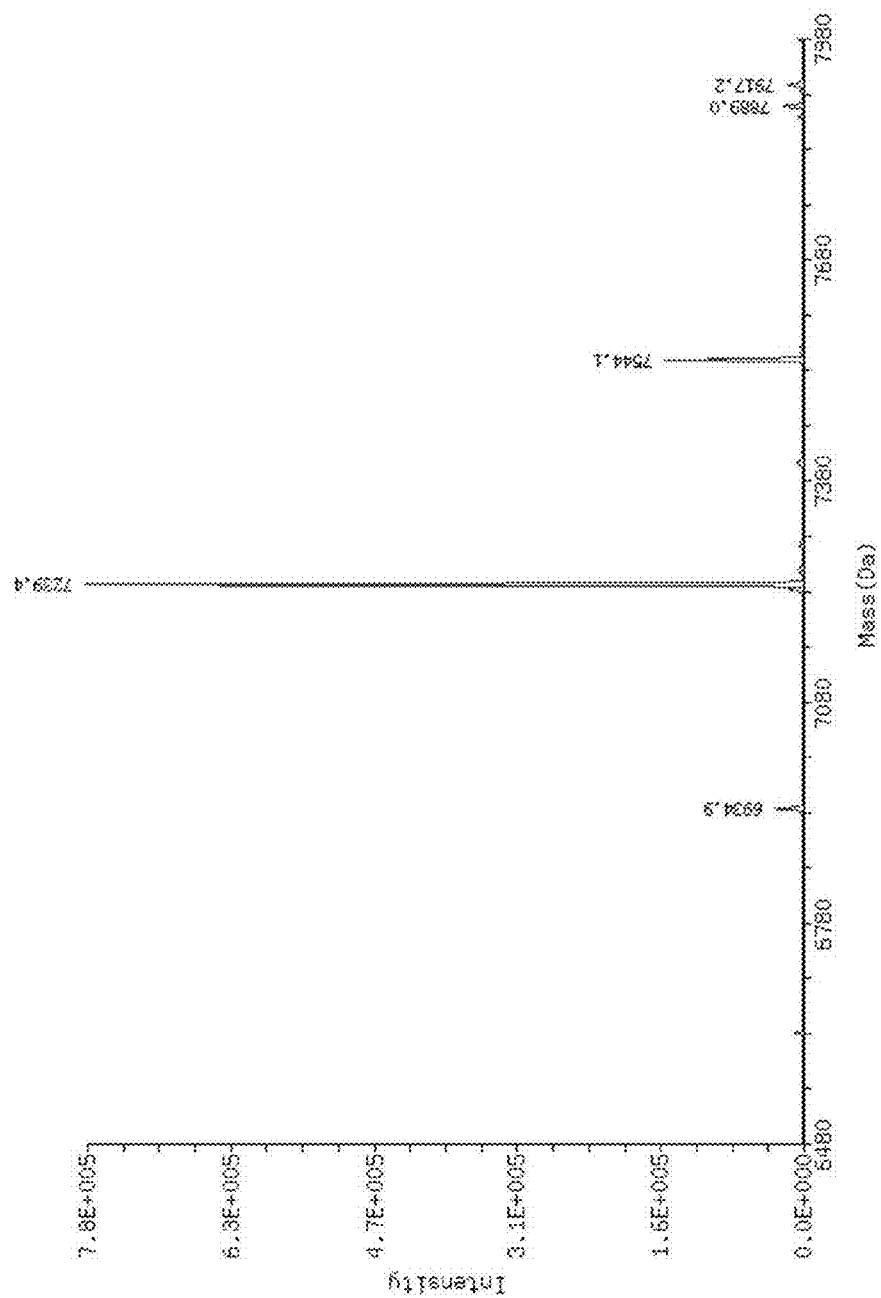
FIG. 3C. Zoomed deconvoluted mass spectrometric analysis of a desalted unbound oligonucleotide.
Figure 4B:
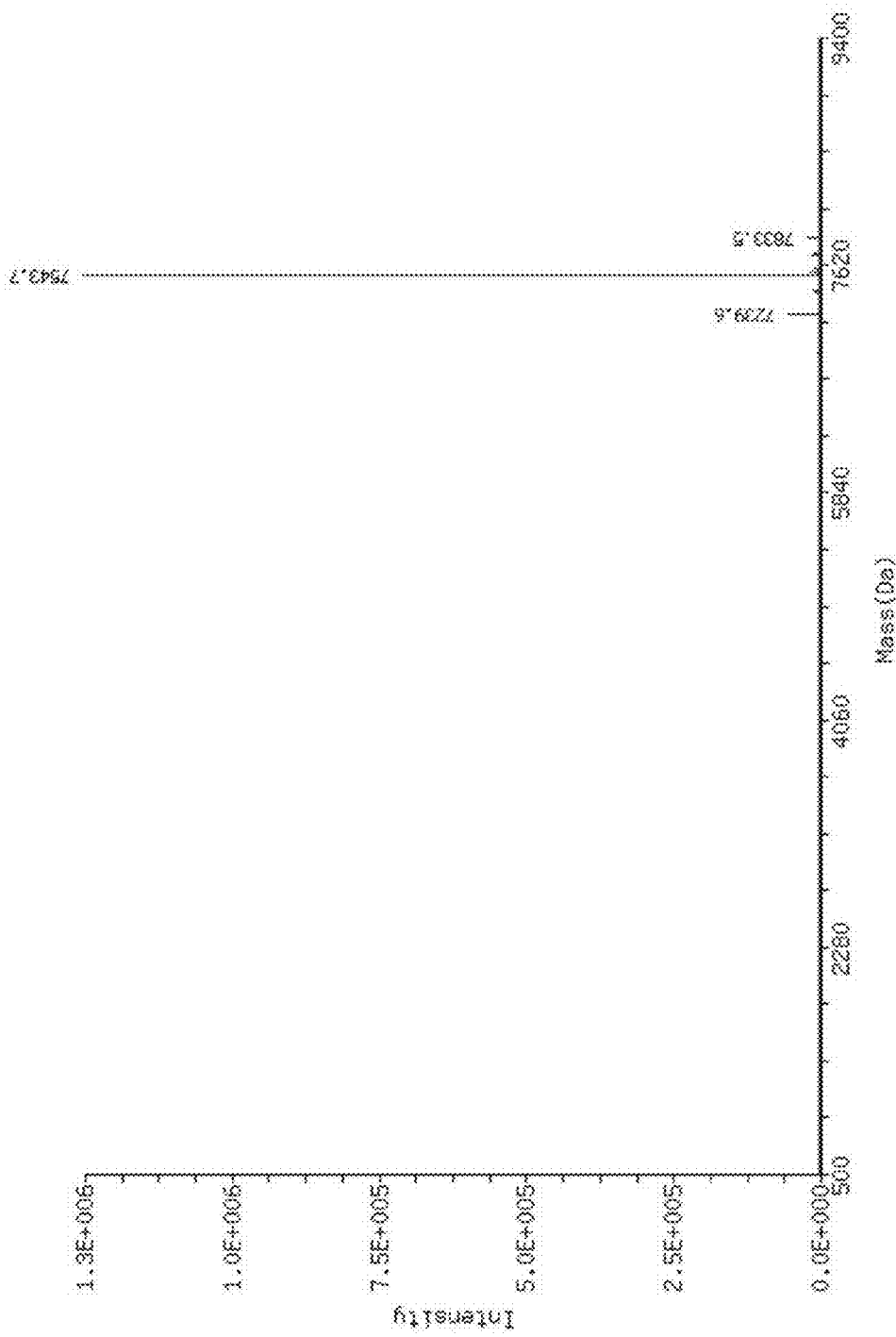
FIG. 4B. Deconvoluted mass spectrometric analysis of a desalted purified oligonucleotide.
Figure 4C:
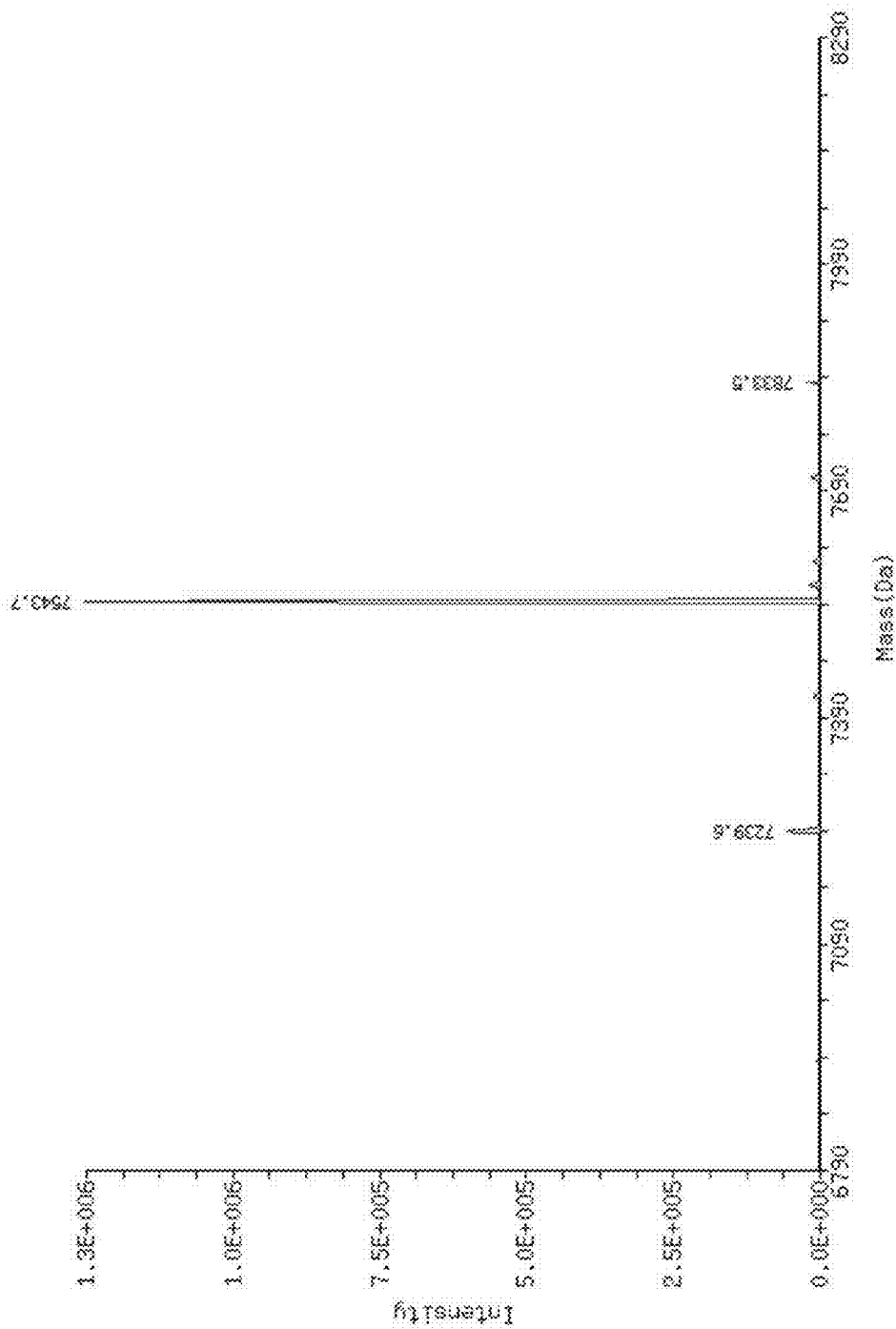
FIG. 4C. Zoomed deconvoluted mass spectrometric analysis of a desalted purified oligonucleotide.

Mass spectrometry was performed on the unbound and purified fractions. Mass spec data of the unbound fraction (FIGS. 3A-3C) indicated a purity of 78.5% N-1 species (dT 24-mer; target mass 7238.7 Da; observed mass 7239.4 Da), with the remainder consisting of a small amount of 4FB-DMT-OFF full-length product (dT 25-mer; target mass 7542.9 Da; observed mass 7544.1 Da) and N-2 (dT 23-mer; target mass 6934.5 Da; observed mass 6934.9 Da), as well as shorter N-X sequences. Mass spec analysis of the purified (capture and release) oligonucleotide sample (FIGS. 4A-4C) indicated a purity of 94.6% full-length 25-mer dT product (target mass 7542.9 Da; observed mass 7543.7 Da), with a minor peak corresponding to N-1 (target mass 7238.7 Da; observed mass 7239.6 Da).

Figure 5A:
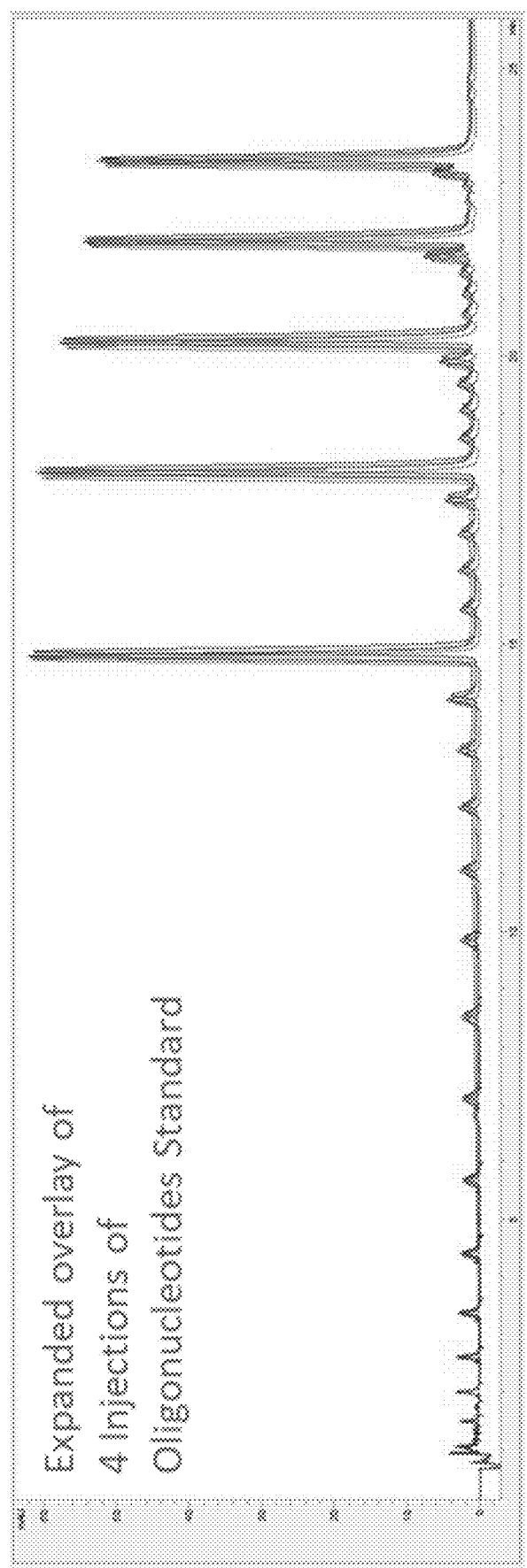
FIG. 5A. Repeatability of four independent IP-UPLC MassPREP™ standard injections.
Figure 5B:
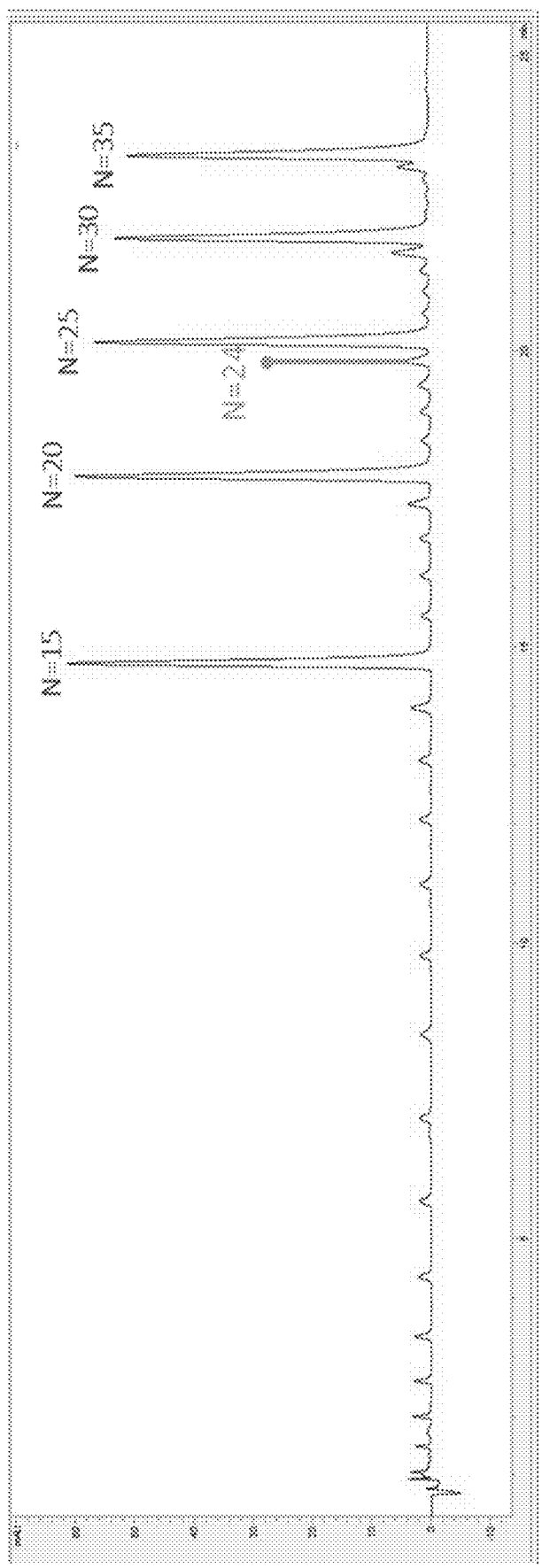
FIG. 5B. Annotation of IP-UPLC MassPREP™ oligonucleotide dT standard.
Figure 6:
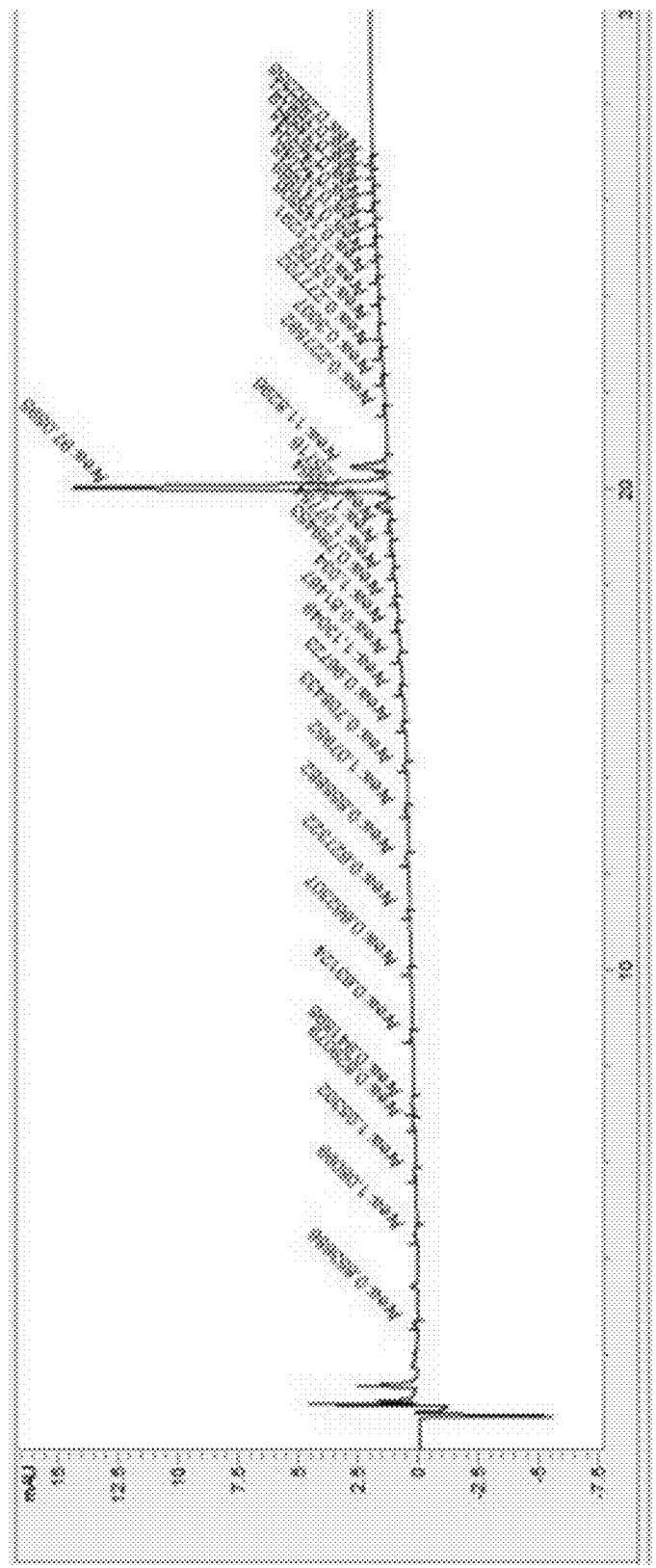
FIG. 6. IP-UPLC analysis of crude (4FB-DMT-ON) desalted 25-mer dT oligonucleotide.
Figure 6:
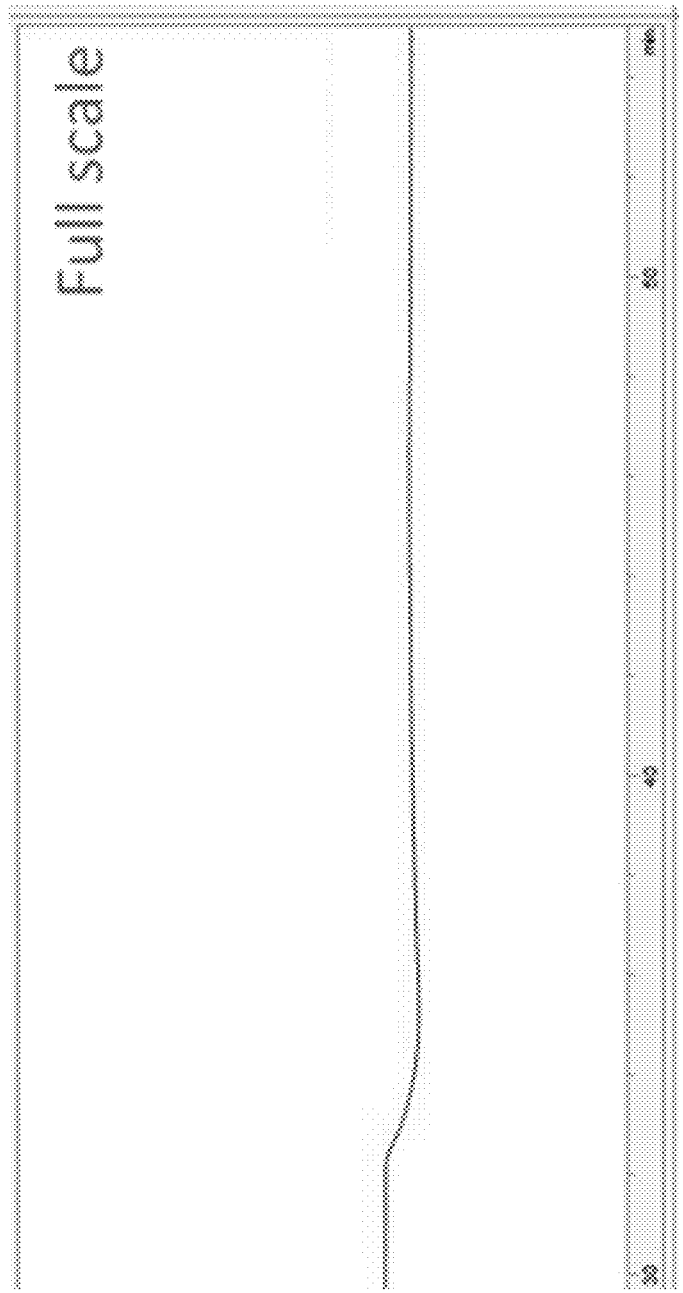
Figure 7:
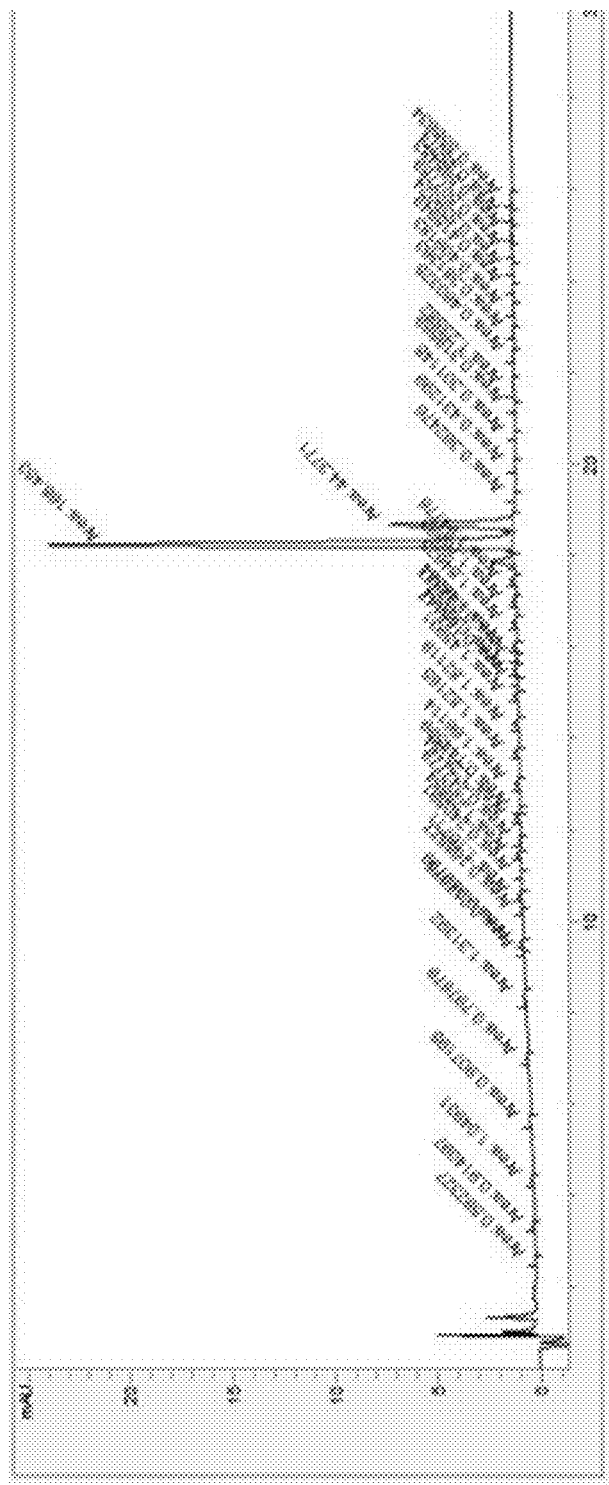
FIG. 7. IP-UPLC analysis of unbound desalted 25-mer dT oligonucleotide.
Figure 7:
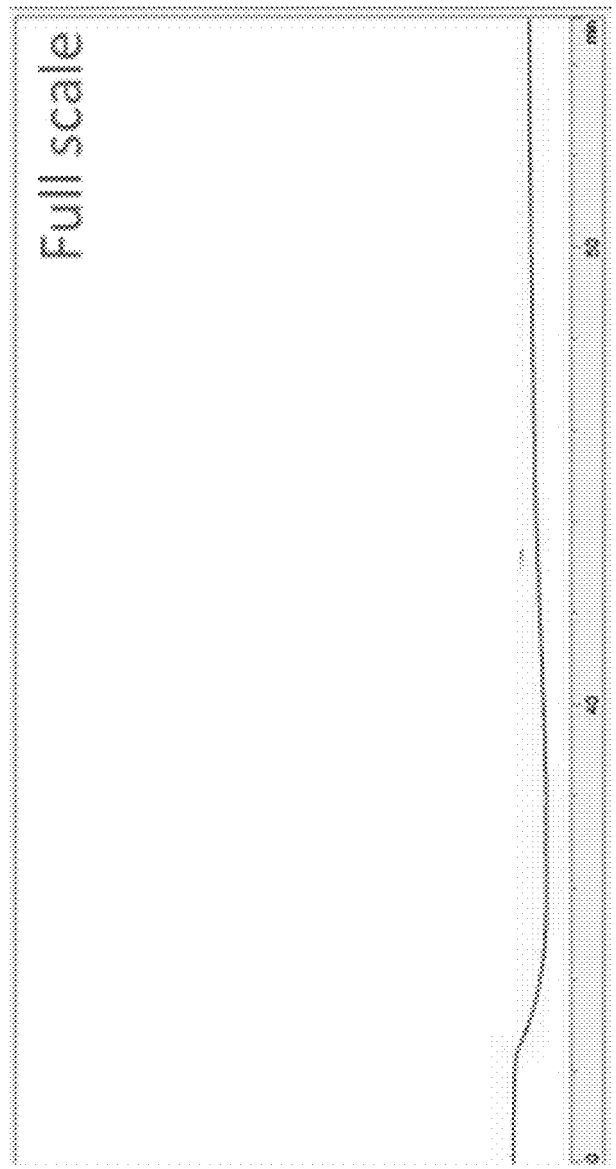
Figure 8:
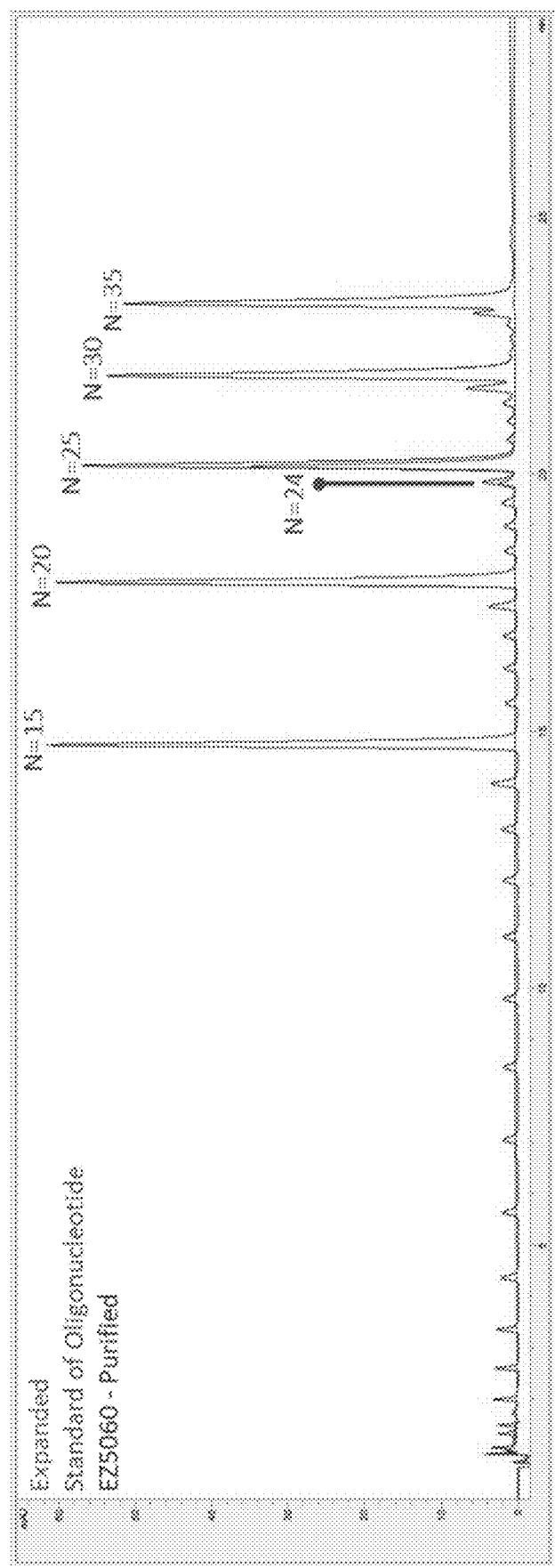
FIG. 8. IP-UPLC analysis of purified desalted 25-mer dT oligonucleotide overlaid with MassPREP™ Oligo dT standard.

Ion-pairing ultra-performance liquid chromatography (IP-UPLC) was performed on the crude (unpurified) oligonucleotide, and the unbound and purified fractions, along with a poly-dT oligonucleotide standard (MassPREP™ oligonucleotide standard; Waters Corporation; catalog #: 186004135) containing equimolar amounts of 15, 20, 25, 30, and 35 nucleotide long oligodeoxythymidine. An Agilent UPLC 1290 Infinity II Series with UV/PDA detector running ChemStation, Rev. C.01.07[27], was used for each analysis. The column was a Waters ACQUITY UPLC BEH C18, 2.1 mm×50 mm, 1.7 µm particle high-resolution column. FIG. 5A illustrates the repeatability of four independent injections of poly-dT MassPREP™ oligonucleotide standards, and FIG. 5B is annotated with the number of dT nucleotides (major peaks are 15, 20, 25, 30, and 35 nucleotides, respectively). FIG. 6 depicts IP-UPLC analysis of crude (4FB-DMT-ON) desalted 25-mer dT oligonucleotide. Failure sequences of N-2 and lower molecular weight are apparent in this analysis, which were not clearly resolved by MS. IP-UPLC analysis of the desalted unbound fraction (FIG. 7) shows an increase in the abundance of failure sequences, and a shift to lower retention time of the main peaks corresponding to N-1 and N-2 truncation products, as expected. The IP-UPLC chromatogram of purified desalted 25-mer dT oligonucleotide (FIG. 8) is devoid of failure sequences, except for a relatively small N-1 peak composing 5.5% of the eluted product. This chromatogram was overlaid with MassPREP™ standard, clearly showing the majority of purified product was the desired full-length 25-mer dT oligonucleotide.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A reagent compound having a structure:

T'-C'-P' wherein T' is a modified trityl protecting group comprising a selectively-reactive linker moiety, C' is a connecting moiety, and P' is a phosphoramidite or phosphoramidate, wherein the selectively-reactive linker moiety comprises an aliphatic or aromatic aldehyde or ketone, an aliphatic or aromatic hydrazide, an aliphatic or aromatic hydrazine, an oxyamino group, or a component of a click reaction.

2. The reagent compound of claim 1, wherein T' has a structure:

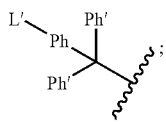

wherein L' comprises the selectively-reactive linker moiety, Ph is an optionally substituted phenylene moiety, and each Ph' is independently an optionally substituted phenyl group.

3. The reagent compound of claim 2, wherein each Ph' is independently substituted with one or more $C_1$-$C_4$ alkoxy groups, one or more $C_1$-$C_4$ alkyl groups, or a combination of $C_1$-$C_4$ alkoxy groups and $C_1$-$C_4$ alkyl groups.

4. The reagent compound of claim 3, having a structure:

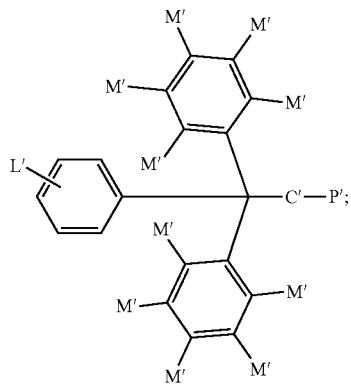

wherein each M' is independently a $C_1$-$C_4$ alkoxy group, a $C_1$-$C_4$ alkyl group, —H, or a combination thereof.

5. The reagent compound of claim 4, having a structure:

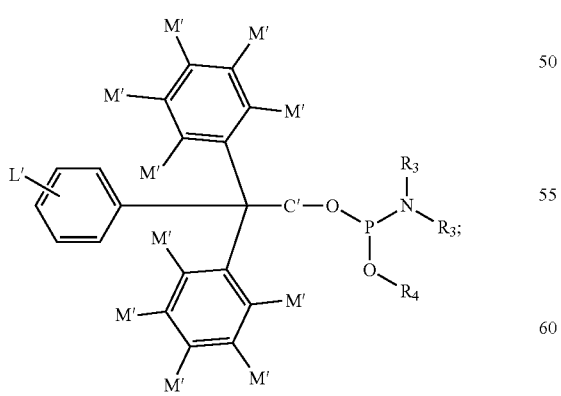

wherein each $R_3$ is independently a $C_1$-$C_6$ alkyl group, and $R_4$ is an optionally-substituted $C_1$-$C_6$ alkyl group or a saccharide-substituted polyethylene glycol group.

6. The reagent compound of claim 5, having a structure:

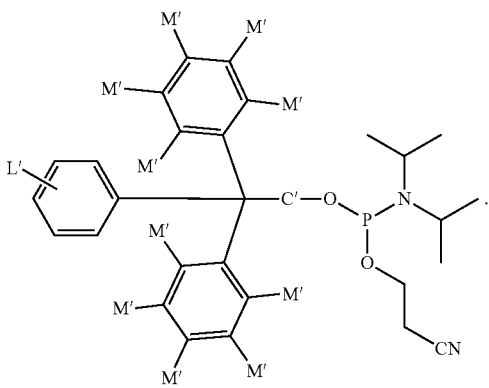

7. The reagent compound of claim 6, wherein at least one M' is a methoxy group.

8. The reagent compound of claim 7, having a structure:

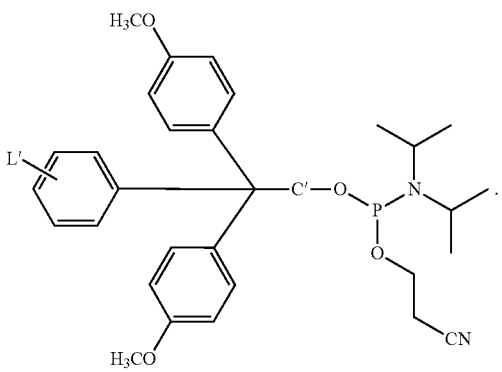

9. The reagent compound of claim 1, wherein the connecting moiety comprises a nucleoside residue, a locked nucleoside residue, a morpholino nucleoside residue, a polyethylene glycol residue, or a linker residue.

10. The reagent compound of claim 9, wherein the connecting moiety comprises a nucleoside residue or a locked nucleoside residue.

11. The reagent compound of claim 10, having a structure:

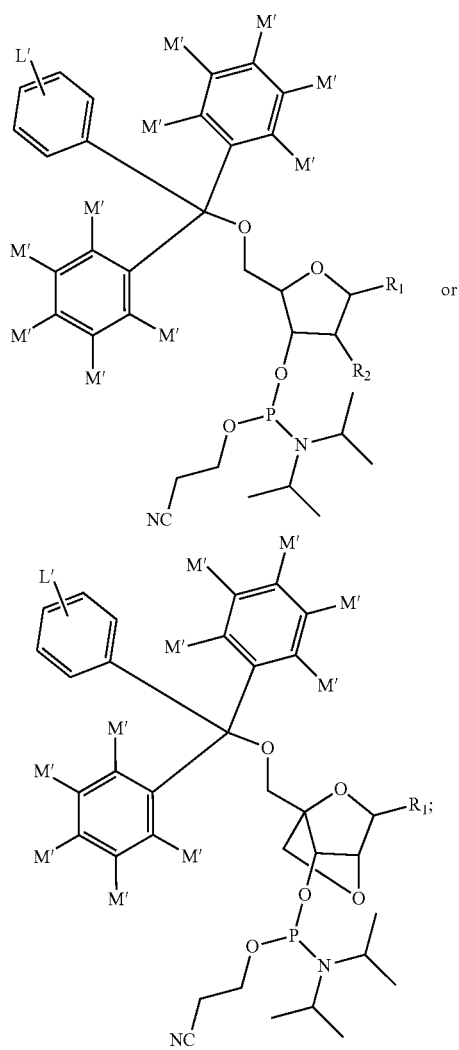

or wherein R₁ is —H, a nucleobase, a protected nucleobase, or a modified nucleobase, and R₂ is —H, -hydroxyl, protected -hydroxyl, modified -hydroxyl, or -halo.

12. The reagent compound of claim 11, wherein R₂ is —H, -hydroxyl, protected -hydroxyl, —OCH₃,

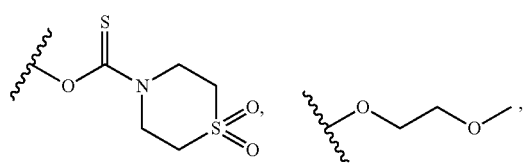

or -fluoro.

13. The reagent compound of claim 9, wherein the connecting moiety comprises a linker residue.

14. The reagent compound of claim 13, wherein the linker residue comprises an optionally substituted —C$_{1-8}$-alkanediyl-, wherein each carbon atom is optionally replaced with an optionally substituted heteroatom.

15. The reagent compound of claim 14, wherein the linker residue comprises:

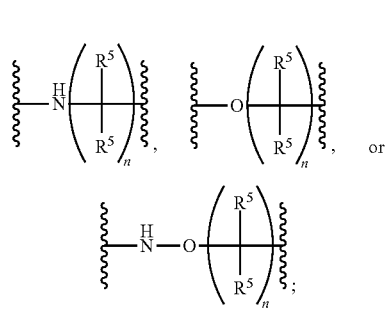

wherein n is 1-6 and each R₅ is independently —H, C$_{1-3}$-alkyl, C$_{1-3}$-carboxylate, C$_{1-3}$-alkyl-C$_{1-3}$-carboxylate, C$_{1-3}$-alkoxy, -halo, -nitro, -amino, -amido, or -hydroxyl.

16. The reagent compound of claim 15, wherein the linker residue comprises:

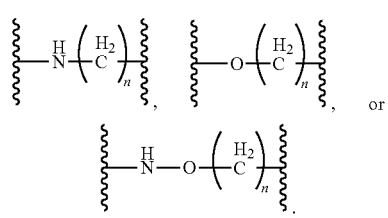

17. The reagent compound of claim 16, wherein the linker residue comprises:

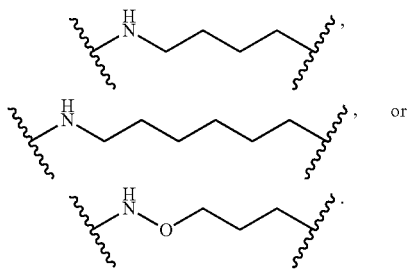

18. The reagent compound of claim 14, wherein the linker residue comprises:

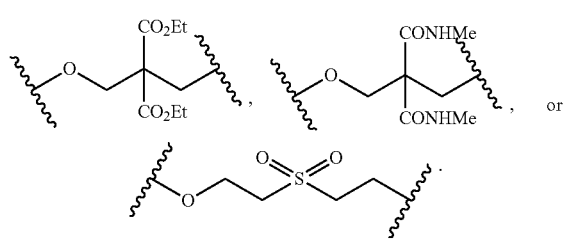

19. The reagent compound of claim 9, wherein the connecting moiety comprises a polyethylene glycol residue.

20. The reagent compound of claim 19, wherein the polyethylene glycol residue comprises a structure:
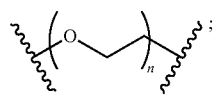
wherein n is from 1 to 20.
21. The reagent compound of claim 1, wherein the selectively-reactive linker moiety comprises:
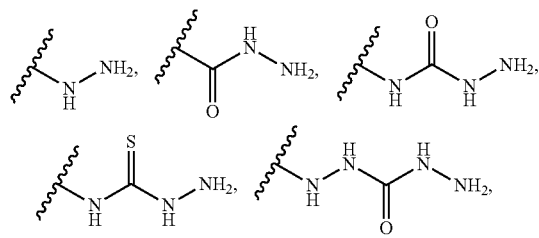
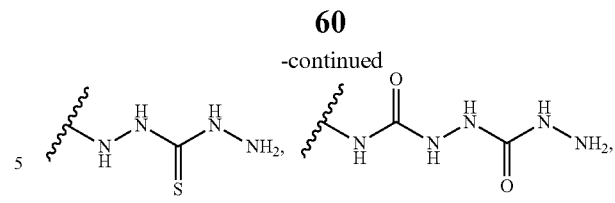
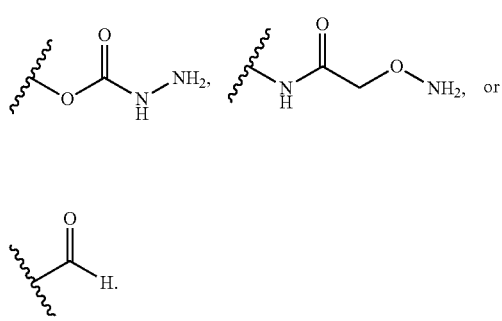
* * * * *